United States Patent [19]

van den Broeck et al.

[11] Patent Number: 5,358,864

[45] Date of Patent: Oct. 25, 1994

[54] CLONING AND EXPRESSION OF XYLANASE GENES FROM FUNGAL ORIGIN

[75] Inventors: Henriette C. van den Broeck, Wageninagen; Leendert H. de Graaff, Arnhem; Jan D. R. Hille, Bergen op Zoom; Albert J. J. van Ooyen, Voorburg; Jacob Visser, Wageningen; Abraham Harder, Berkel en Rodenrijs, all of Netherlands

[73] Assignee: Gist-Brocades, N.V., Delft, Netherlands

[21] Appl. No.: 842,349

[22] PCT Filed: Jul. 24, 1991

[86] PCT No.: PCT/NL91/00137

§ 371 Date: Apr. 27, 1992

§ 102(e) Date: Apr. 27, 1992

[87] PCT Pub. No.: WO92/01793

PCT Pub. Date: Feb. 6, 1992

[30] Foreign Application Priority Data

Jul. 24, 1990 [EP]  European Pat. Off. ........ 90202020.5

[51] Int. Cl.[5] .......................... C12N 9/42; C12N 9/24; C07H 21/04; C12P 21/06
[52] U.S. Cl. ....................... 435/209; 426/10; 426/20; 426/635; 162/87; 435/69.1; 435/200; 435/252.3; 435/320.1; 536/22.1; 536/23.1; 536/23.2; 536/23.4; 536/23.74; 536/24.1
[58] Field of Search ............ 426/10, 20, 635; 162/87; 435/69.1, 320.1, 252.3, 201, 202, 203, 209; 536/22.1, 23.1, 23.2, 23.4, 23.74, 24.1

[56] References Cited

U.S. PATENT DOCUMENTS 4,990,343  2/1991  Haarasilta et al. .................... 426/10

FOREIGN PATENT DOCUMENTS 021138  10/1984  European Pat. Off. .
0227159  1/1987  European Pat. Off. .
WO91/19782  12/1991  PCT Int'l Appl. .

OTHER PUBLICATIONS

Fournier et al. "Purification and Characterization . . . " Biotech & Bioengin. 27: pp. 539–546 1985.
Glover "Principles of cloning DNA" Gene Cloning pp. 1–20 1984.
Glover "Expression of cloned DNA in *E. coli* plasmid" Gene Cloning pp. 110"127.
Chesson A., *Recent Advances in Animal Nutrition* (1987) Haresign W. and Cole, D. J. A., eds., Butterworths, London, Chapter 6, pp. 71–89.
Carré B., et al., *J. Sci. Food Agric.* (1986) 37:341–351.
McCleary B. V., et al., *Adv. Carb. Chem. and Biochem.* Tipson, R. S., et al., eds., (1986) 44:147–276.
Wong K., et al., *Microbiol. Rev.* (1988) 52(3):305–317.
Woodward J., *Topics in Enzyme Ferment. Biotechnol.* Wiseman, A., ed., (1984) 8:9–30.
Dekker R., et al., *Adv. Carb. Chem. and Biochem.* Tipson, R. S. et al., eds., (1977) 32:278–353.

*Primary Examiner*—Charles L. Patterson, Jr.
*Assistant Examiner*—Hyosuk Kim
*Attorney, Agent, or Firm*—Morrison & Foerster

[57] ABSTRACT

Methods and expression constructs are provided for the cloning and overexpression of xylanases of fungai origin in a selected microbial host cell. Xylanases of fungal origin generally have lower pH optima and remain stable over a broader pH range than do xylanases of bacterial origin. The present invention provides for the high level production of fungal xylanases which are may be used in a variety of industrial applications requiring xylanase activity at a low pH.

19 Claims, 23 Drawing Sheets

N-terminal amino acid sequence of the

_Aspergillus tubigensis_ XYL A protein

```
  1              5                10
Ala-Gly-Ile-Asn-Tyr-Val-Gln-Asn-Tyr-Asn     (Formula 1)
```

Oligonucleotides are derived from residue 4 (Asn) to residue 10 (Asn) complementary to the corresponding mRNA:

```
                    G  A  T      G
AB801      5'  TT TA TT TGAAC TAATT  3'
                    A  G  C      A

G  A  T      G
AB802      5'  TT TA TT TGGAC TAATT  3'
                    A  G  C      A

G  A  T      G
AB803      5'  TT TA TT TGCAC TAATT  3'
                    A  G  C      A

G  A  T      G
AB804      5'  TT TA TT TGAAC TAGTT  3'
                    A  G  C      A

G  A  T      G
AB805      5'  TT TA TT TGGAC TAGTT  3'
                    A  G  C      A

G  A  T      G
AB806      5'  TT TA TT TGCAC TAGTT  3'
                    A  G  C      A
```

N-terminal amino acid sequence of an internal 19 kDa fragment of the Aspergillus tubigensis XYL A protein, digested with the S. aureus V8 endopeptidase:

```
 1               5               10              14
Tyr-Tyr-Ile-Val-Glu-Asp-Tyr-Gly- X -Tyr-Asn-Pro-Cys-(Ser)
```
(Formula 2)

```
 1               5               10              14
Tyr-Tyr-Ile-Val-Glu-Asp-Tyr-Gly-(Ser)-Tyr-Asn-Pro-Cys-(Ser)
```
(Formula 3)

Oligonucleotides are derived from residue 2 (Tyr) to residue 7 (Tyr) complementary to the corresponding mRNA:

```
            A   T      A  A  A
AB1255  5' TA  TC TCNACGAT TA TA 3'
            G   C      G  C
                       T  G  G
```

FIG. 8A

Sequence listing

SEQ ID NO: 1

SEQUENCE TYPE: Nucleotide with corresponding polypeptide

SEQUENCE LENGTH: 2054 base pairs

STRANDNESS: double

TOPOLOGY: linear

MOLECULE TYPE: genomic DNA

ORIGINAL SOURCE ORGANISM: Aspergillus tubigensis

IMMEDIATE EXPERIMENTAL SOURCE: pIM100 in E.coli
JM101 (CBS 322.90)

FEATURES: from 848 to 854 bp potential TATA signal
from 950 to 1632 coding sequence
from 1179 to 1230 intron 1
from 950 to 1031 prepropeptide
from 1031 to 1632 mature peptide
from 594 to 748 region involved in induction
from 618 to 632 and from 637 to 651 and from 656 to 672 repeat PROPERTIES: Aspergillus niger endoxylanase A (xln A) gene

| | | | | | |
|---|---|---|---|---|---|
|AACGTCTGCA|GTCCCGTACT|GTTACCAAA|ATGCCAGGCC|ACTGGTGGAT|ATACAACTTT|60
|GTAATACGTT|GCCGGAGTCA|GCCCCTACTC|CCTGATGGGT|TCCCACTCCC|TAGTTACTTC|120
|CTACTGGGTA|GTAGGCTCCT|AGAGTGGGGT|AAAGTTTGCC|AAGGGTTTAG|CCCCAGTCTT|180
|GTTTATGCTT|GGCTAGGCAG|GACCTGGGTA|AGTTGATGGC|TCCTGCATTC|CTACCTGAGT|240
|ATTCCAGCT|ATAAGGCAGA|TCTTCAGCGA|GTCCGGATGG|TCCGCGCCGA|300
|GGTTGACCCT|GCCTTCATCA|CCTACACAAA|GAACTCCTCG|GCCAACTCCC|GGTGGCCTTC|360
|GAGCTCCAAA|GTACCTTCGC|GACCTTTGGC|CAGTGTTTCT|CCGCAGGCGTT|ACTGAGCCTA|420
|AGGCTTGCTA|CAATAAATAA|AGAGACATAA|CCTTGCAGTA|CATACGTCTT|GTATGAGCGA|480
|GGAACTGTGT|TCAGTAGTAG|ATCAGTGGGT|ACATAATCAT|GAACATGACT|TCTGAGCCAG|540
|AAAACCTTCT|GCAGGGAACC|GGTGAAGAAA|CCCCACTTCC|CCGCCTCCAC|TAACTGCAGC|600
|CCCTTTATCC|GCCTGCCGTC|CATTTAGCCA|AATGTAGTCC|ATTTAGCCAA|GTGCGGTCCA|660
|TTTAGCCAAG|TCCAGTGCTT|AGGTTGGTGG|CTACACAGGA|AACGGCCATG|AATGTAGACA|720
|CAACTATAGA|ACTGTCCCTA|GAAATAGGCT|CGAGGTTGTT|AGAGCGTTTA|AGGTGATGCG|780
|GCAAAATGCA|TATGACTGAG|TTGCTTCAAC|GTGCAGGGGA|AAGGGATAAA|TAGTCTTTT|840
|CGCAGAATAT|AAATAGAGGT|AGAGCGGGCT|CGGCAGCAATA|TTGACCAGGA|CAGGGCTTCT|900
|TTTCCAGTTG|CATACATCCA|TTCACAGCAT|TCAGCTTTCT|TCAATCATC|ATG AAG GTC|958
| | | | | |Met Lys Val|
| | | | | |-25|

FIG. 8B

```
ACT GCG GCT TTT GCA GGT CTT TTG GTC ACG GCA TTC GCC GCT CCT GCC   1006
Thr Ala Ala Phe Ala Gly Leu Leu Val Thr Ala Phe Ala Ala Pro Ala
                -20                     -15                -10

CCA GAA CCT GAT CTG GTG TCG CGA AGT GCC GGT ATC AAC TAC GTG CAA   1054
Pro Glu Pro Asp Leu Val Ser Arg Ser Ala Gly Ile Asn Tyr Val Gln
            -5                         1                 5

AAC TAC AAC GGC AAC CTT GGT GAT TTC ACC TAC GAC GAG AGT GCC GGA   1102
Asn Tyr Asn Gly Asn Leu Gly Asp Phe Thr Tyr Asp Glu Ser Ala Gly
             10                     15                  20

ACA TTT TCC ATG TAC TGG GAA GAT GGA GTG AGC TCC GAC TTT GTC GTT   1150
Thr Phe Ser Met Tyr Trp Glu Asp Gly Val Ser Ser Asp Phe Val Val
         25                      30                  35        40

GGT CTG GGC TGG ACC ACT GGT TCT TCT AA GTGAGTGACT GTATCTTTA        1199
Gly Leu Gly Trp Thr Thr Gly Ser Ser Asn
            45                       50
```

FIG. 8C

```
ACCAAGGTCT AGGATCTAAC GTCTTTCAG C GCT ATC ACC. TAC TCT GCC GAA         1250
                                  Ala Ile Thr Tyr Ser Ala Glu
                                               55

TAC AGC GCT TCT GGC TCC GCT TCC TAC CTC GCT GTG TAC GGC TGG GTC        1298
Tyr Ser Ala Ser Gly Ser Ala Ser Tyr Leu Ala Val Tyr Gly Trp Val
             60                      65                    70

AAC TAT CCT CAA GCT GAG TAC TAC ATC GTC GAG GAT TAC GGT GAT TAT        1346
Asn Tyr Pro Gln Ala Glu Tyr Tyr Ile Val Glu Asp Tyr Gly Asp Tyr
     75                      80                      85

AAC CCT TGC AGT TCG GCC ACA AGC CTT GGT ACC GTG TAC TCT GAT GGA        1395
Asn Pro Cys Ser Ser Ala Thr Ser Leu Gly Thr Val Tyr Ser Asp Gly
         90                      95                     100         105

AGC ACC TAC CAA GTC TGC ACC GAC ACT CGA ACA AAC GAA CCG TCC ATC        1442
Ser Thr Tyr Gln Val Cys Thr Asp Thr Arg Thr Asn Glu Pro Ser Ile
             110                     115                    120
```

```
ACG GGA AGA AGC ACG TTC ACG CAG TAC TTC TCC GTT CGA GAG AGC ACG    1490
Thr Gly Thr Ser Thr Phe Thr Gln Tyr Phe Ser Val Arg Glu Ser Thr
            125                 130                 135

GCG ACA TCT GGA ACG GTG ACT GTT GCC AAC CAT TTC AAC TTC TGG GCG    1538
Arg Thr Ser Gly Thr Val Thr Val Ala Asn His Phe Asn Phe Trp Ala
            140                 145                 150

CAG CAT GGG TTC GGC AAT ACG GAC TTC AAT TAT CAG GTC GTG GCG GTG    1586
His His Gly Phe Gly Asn Ser Asp Phe Asn Tyr Gln Val Val Ala Val
            155                 160                 165

GAA GCA TGG AGC GGT GCT GGC AGC GCT AGT GTC ACA ATC TCT TCT TGA    1634
Glu Ala Trp Ser Gly Ala Gly Ser Ala Ser Val Thr Ile Ser Ser
170                 175                 180

GAGATTAGTG CCCTAGTAGT CGGAAGATAT CAACGCGGCA GTTTGCTCTC AGGTGGTGTG    1694
ATGATCGGAT CCGGTCTCTG GGGTTACATT GAGGCTGTAT AAGTTGTTGT GGGGCCGAGC    1754
TGTCAGCGGC TGCGTTTTCA GCTTGCACAG ATAATCAACT CTCGTTTTCT ATCTCTTGCG    1814
TTTCCTCGCT GCTTATCCTA TCCATAGATA ATTATTTTGC CCACTACCAC AACTTGTTCG    1874
GTCGCAGTAG TCACTCCGAG CAAGGCATTG GGAAATGGGG GATGCGGGGT GCTGCGTACC    1934
CTCTAACCTA GGGCATTTTA AAGGATATTT ACCCTCCAGA TATTCTATAG ATACAGACTT    1994
CTTAGGACTG CGGGTAATAT AGAGAGCGAA ATTTCTACAG TTCGATGCAG TTCAATGCGA    2054
```

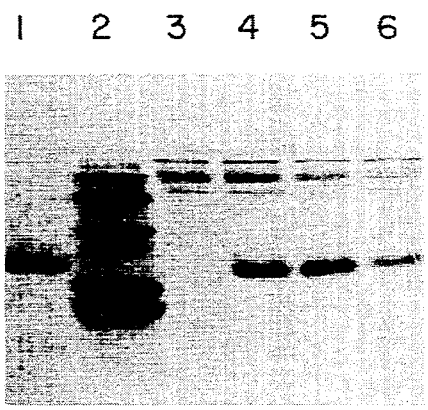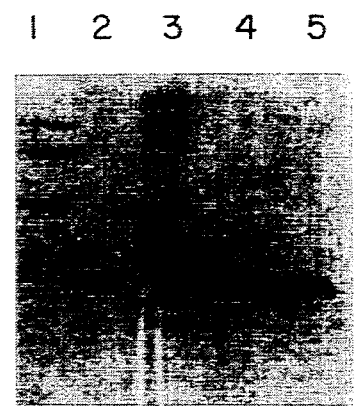
FIG.10A  FIG.10B
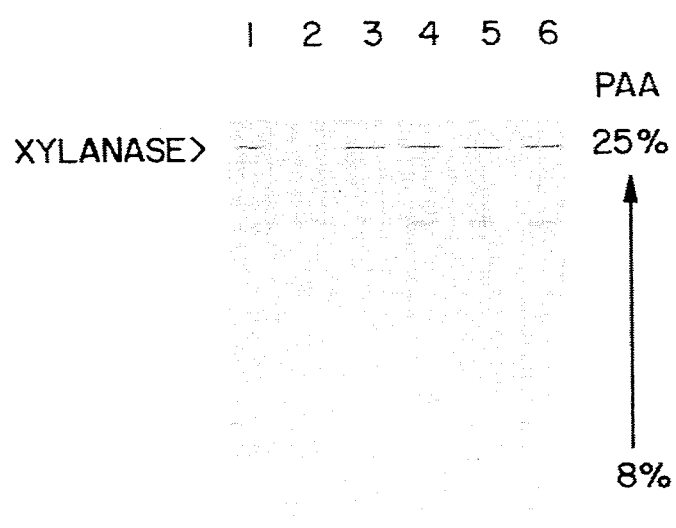
FIG.11A  FIG.11B

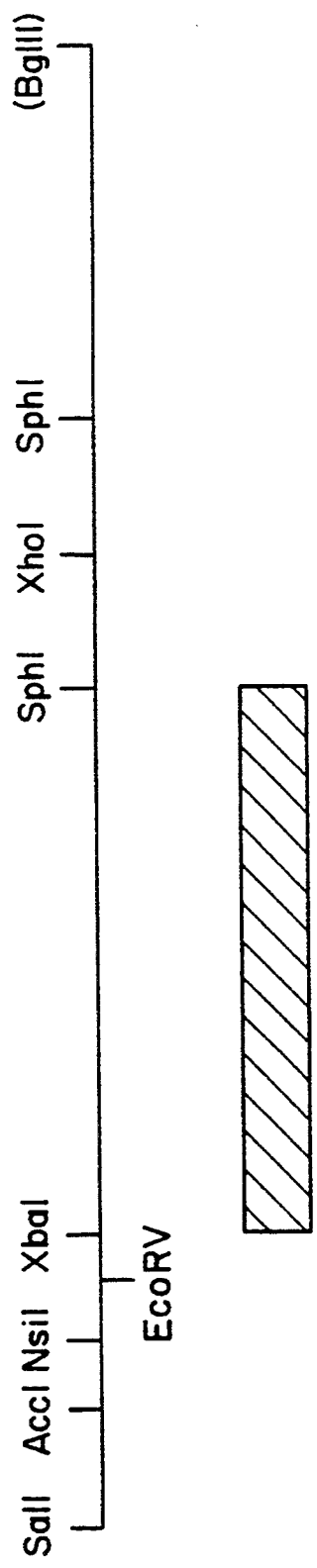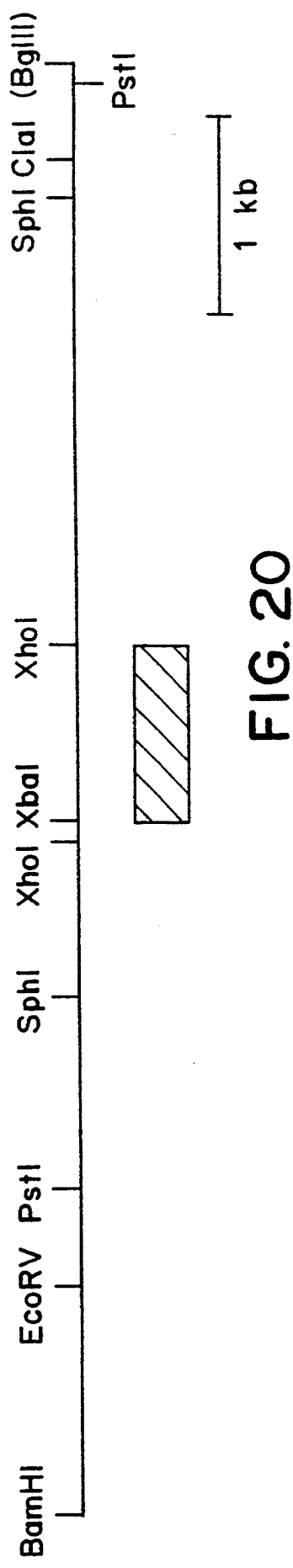

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 2055 base pairs
( B ) TYPE: nucleic acid
( C ) STRANDEDNESS: single
( D ) TOPOLOGY: linear ( i x ) FEATURE:
 ( A ) NAME/KEY: CDS
 ( B ) LOCATION: join(950..1180, 1231..1632)

( i x ) FEATURE:
 ( A ) NAME/KEY: matpeptide
 ( B ) LOCATION: 1031

( x i ) SEQUENCE DESCRIPTION: SEQ ID NO:1:

| | | | | | |
|---|---|---|---|---|---|
| AACGTCTGCA | GTCCCGTACT | GTTTACCAAA | ATGCCAGGCC | ACTGGTGGAT | ATACAACTTT | 60
| GTAATACGTT | GCCGGAGTCA | GCCCCTACTC | CCTGATGGGT | TCCCACTCCC | TAGTTACTTC | 120
| CTACTGGGTA | GTAGGCTCCT | AGAGTGGGGT | AAAGTTTGCC | AAGGGTTTAG | CCCCAGTCTT | 180
| GTTTATGCTT | GGCTAGGCAG | GACCTGGGTA | AGTTGATGGC | TCCTGCATTC | CTACCTGAGT | 240
| ATTTCCAGCT | ATAAGCGAGA | TTTGCCATAC | TCTTCAGCGA | GTCCGGATGG | TCCGCGCCGA | 300
| GGTTGACCCT | GCCTTCATCA | CCTACACAAA | GAACTCCTCG | GCCAACTCCC | GGTGGCCTTC | 360
| GAGCTCCAAA | GTACCTTCGC | GACCTTTGGC | CAGTGTTTCT | CGCAGCGTTT | ACTGAGCCTA | 420
| AGGCTTGCTA | CAATAAATAA | AGAGACATAA | CCTTGCAGTA | CATACGTCTT | GTATGAGCGA | 480
| GGAACTGTGT | TCAGTAGTAG | ATCAGTGGGT | ACATAATCAT | GAACATGACT | TCTGAGCCAG | 540
| AAAACCTTCT | GCAGGGAACC | GGTGAAGAAA | CCCCACTTCC | CCGCCTCCAC | TAACTGCAGC | 600
| CCCTTTATCC | GCCTGCCGTC | CATTTAGCCA | AATGTAGTCC | ATTTAGCCAA | GTGCGGTCCA | 660
| TTTAGCCAAG | TCCAGTGCTT | AGGTTGGTGG | CTACACAGGA | AACGGCCATG | AATGTAGACA | 720
| CAACTATAGA | ACTGTCCCTA | GAAATAGGCT | CGAGGTTGTT | AGAGCGTTTA | AGGTGATGCG | 780
| GCAAAATGCA | TATGACTGAG | TTGCTTCAAC | GTGCAGGGGA | AAGGGATAAA | TAGTCTTTTT | 840
| CGCAGAATAT | AAATAGAGGT | AGAGCGGGCT | CGCAGCAATA | TTGACCAGGA | CAGGGCTTCT | 900
| TTTCCAGTTG | CATACATCCA | TTCACAGCAT | TCAGCTTTCT | TCAATCATC ATG AAG | | 955

```
                                                                       Met Lys
                                                                        -27

GTC ACT GCG GCT TTT GCA GGT CTT TTG GTC ACG GCA TTC GCC GCT CCT        1003
Val Thr Ala Ala Phe Ala Gly Leu Leu Val Thr Ala Phe Ala Ala Pro
-25             -20                 -15                 -10

GCC CCA GAA CCT GAT CTG GTG TCG CGA AGT GCC GGT ATC AAC TAC GTG        1051
Ala Pro Glu Pro Asp Leu Val Ser Arg Ser Ala Gly Ile Asn Tyr Val
            -5                   1                   5

CAA AAC TAC AAC GGC AAC CTT GGT GAT TTC ACC TAC GAC GAG AGT GCC        1099
Gln Asn Tyr Asn Gly Asn Leu Gly Asp Phe Thr Tyr Asp Glu Ser Ala
            10                  15                  20

GGA ACA TTT TCC ATG TAC TGG GAA GAT GGA GTG AGC TCC GAC TTT GTC        1147
Gly Thr Phe Ser Met Tyr Trp Glu Asp Gly Val Ser Ser Asp Phe Val
    25                  30                  35

GTT GGT CTG GGC TGG ACC ACT GGT TCT TCT AAC GTGAGTGACT GTATTCTTA       1200
Val Gly Leu Gly Trp Thr Thr Gly Ser Ser Asn
40                  45                  50

ACCAAGGTCT AGGATCTAAC GTCTTTCAGC GCT ATC ACC TAC TCT GCC GAA TAC       1254
                                Ala Ile Thr Tyr Ser Ala Glu Tyr
                                                55

AGC GCT TCT GGC TCC GCT TCC TAC CTC GCT GTG TAC GGC TGG GTC AAC        1302
Ser Ala Ser Gly Ser Ala Ser Tyr Leu Ala Val Tyr Gly Trp Val Asn
    60                  65                  70

TAT CCT CAA GCT GAG TAC TAC ATC GTC GAG GAT TAC GGT GAT TAT AAC        1350
Tyr Pro Gln Ala Glu Tyr Tyr Ile Val Glu Asp Tyr Gly Asp Tyr Asn
75                  80                  85                  90

CCT TGC AGT TCG GCC ACA AGC CTT GGT ACC GTG TAC TCT GAT GGA AGC        1398
Pro Cys Ser Ser Ala Thr Ser Leu Gly Thr Val Tyr Ser Asp Gly Ser
            95                  100                 105
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ACC | TAC | CAA | GTC | TGC | ACC | GAC | ACT | CGA | ACA | AAC | GAA | CCG | TCC | ATC | ACG | 1446 |
| Thr | Tyr | Gln<br>110 | Val | Cys | Thr | Asp | Thr | Arg<br>115 | Thr | Asn | Glu | Pro | Ser<br>120 | Ile | Thr |      |
| GGA | AGA | AGC | ACG | TTC | ACG | CAG | TAC | TTC | TCC | GTT | CGA | GAG | AGC | ACG | GCG | 1494 |
| Gly | Arg | Ser<br>125 | Thr | Phe | Thr | Gln | Tyr<br>130 | Phe | Ser | Val | Arg | Glu<br>135 | Ser | Thr | Ala |      |
| ACA | TCT | GGA | ACG | GTG | ACT | GTT | GCC | AAC | CAT | TTC | AAC | TTC | TGG | GCG | CAG | 1542 |
| Thr | Ser | Gly<br>140 | Thr | Val | Thr | Val<br>145 | Ala | Asn | His | Phe | Asn<br>150 | Phe | Trp | Ala | Gln |      |
| CAT | GGG | TTC | GGC | AAT | ACG | GAC | TTC | AAT | TAT | CAG | GTC | GTG | GCG | GTG | GAA | 1590 |
| His<br>155 | Gly | Phe | Gly | Asn | Thr<br>160 | Asp | Phe | Asn | Tyr | Gln<br>165 | Val | Val | Ala | Val | Glu<br>170 |      |
| GCA | TGG | AGC | GGT | GCT | GGC | AGC | GCT | AGT | GTC | ACA | ATC | TCT | TCT |     |     | 1632 |
| Ala | Trp | Ser | Gly | Ala<br>175 | Gly | Ser | Ala | Ser | Val<br>180 | Thr | Ile | Ser | Ser |     |     |      |

```
TGAGAGATTA GTGCCCTAGT AGTCGGAAGA TATCAACGCG GCAGTTTGCT CTCAGGTGGT    1692

GTGATGATCG GATCCGGTCT CTGGGGTTAC ATTGAGGCTG TATAAGTTGT TGTGGGGCCG    1752

AGCTGTCAGC GGCTGCGTTT TCAGCTTGCA CAGATAATCA ACTCTCGTTT TCTATCTCTT    1812

GCGTTCCTC GCTGCTTATC CTATCCATAG ATAATTATTT TGCCCACTAC CACAACTTGT    1872

TCGGTCGCAG TAGTCACTCC GAGCAAGGCA TTGGGAAATG GGGGATGCGG GGTGCTGCGT    1932

ACCCTCTAAC CTAGGGCATT TTAAAGGATA TTTACCCTCC AGATATTCTA TAGATACAGA    1992

CTTCTTAGGA CTGCGGGTAA TATAGAGAGC GAAATTTCTA CAGTTCGATG CAGTTCAATG    2052

CGA                                                                  2055
```

( 2 ) INFORMATION FOR SEQ ID NO:2:

( i ) SEQUENCE CHARACTERISTICS:
      ( A ) LENGTH: 211 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |     |
|-----|-----|-----|-----|-----|-----|-----|-----|-----|-----|-----|-----|-----|-----|-----|
| Met | Lys<br>-27 | Val | Thr<br>-25 | Ala | Ala | Phe | Ala<br>-20 | Gly | Leu | Leu | Val | Thr<br>-15 | Ala | Phe Ala |
| Ala | Pro<br>-10 | Ala | Pro | Glu | Pro | Asp<br>-5 | Leu | Val | Ser | Arg | Ser | Ala<br>1 | Gly | Ile Asn<br>5 |
| Tyr | Val | Gln | Asn | Tyr<br>10 | Asn | Gly | Asn | Leu | Gly<br>15 | Asp | Phe | Thr | Tyr | Asp Glu<br>20 |
| Ser | Ala | Gly | Thr<br>25 | Phe | Ser | Met | Tyr | Trp | Glu<br>30 | Asp | Gly | Val | Ser<br>35 | Ser Asp |
| Phe | Val | Val<br>40 | Gly | Leu | Gly | Trp | Thr<br>45 | Thr | Gly | Ser | Ser | Asn<br>50 | Ala | Ile Thr |
| Tyr | Ser<br>55 | Ala | Glu | Tyr | Ser<br>60 | Ala | Ser | Gly | Ser | Ala<br>65 | Ser | Tyr | Leu | Ala Val |
| Tyr<br>70 | Gly | Trp | Val | Asn | Tyr<br>75 | Pro | Gln | Ala | Glu | Tyr<br>80 | Tyr | Ile | Val | Glu Asp<br>85 |
| Tyr | Gly | Asp | Tyr | Asn<br>90 | Pro | Cys | Ser | Ser | Ala<br>95 | Thr | Ser | Leu | Gly | Thr Val<br>100 |
| Tyr | Ser | Asp | Gly | Ser<br>105 | Thr | Tyr | Gln | Val | Cys<br>110 | Thr | Asp | Thr | Arg | Thr Asn<br>115 |
| Glu | Pro | Ser | Ile | Thr<br>120 | Gly | Arg | Ser | Thr | Phe<br>125 | Thr | Gln | Tyr | Phe | Ser Val<br>130 |
| Arg | Glu | Ser<br>135 | Thr | Ala | Thr | Ser | Gly<br>140 | Thr | Val | Thr | Val | Ala<br>145 | Asn | His Phe |

| Asn | Phe | Trp | Ala | Gln | His | Gly | Phe | Gly | Asn | Thr | Asp | Phe | Asn | Tyr | Gln |
| 150 | | | | | 155 | | | | | 160 | | | | | 165 |

| Val | Val | Ala | Val | Glu | Ala | Trp | Ser | Gly | Ala | Gly | Ser | Ala | Ser | Val | Thr |
| | | | | 170 | | | | | 175 | | | | | 180 | |

Ile Ser Ser ( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

| Ala | Gly | Ile | Asn | Tyr | Val | Gln | Asn | Tyr | Asn |
| 1 | | | | 5 | | | | | 10 |

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: miscdifference
        ( B ) LOCATION: replace(3, "")
        ( D ) OTHER INFORMATION: /note="This position is G or A."

( i x ) FEATURE:
        ( A ) NAME/KEY: miscdifference
        ( B ) LOCATION: replace(6, "")
        ( D ) OTHER INFORMATION: /note="This position is A or G."

( i x ) FEATURE:
        ( A ) NAME/KEY: miscdifference
        ( B ) LOCATION: replace(9, "")
        ( D ) OTHER INFORMATION: /note="This position is T or C."

( i x ) FEATURE:
        ( A ) NAME/KEY: miscdifference
        ( B ) LOCATION: replace(15, "")
        ( D ) OTHER INFORMATION: /note="This position is G or A."

( x i ) SEQUENCE DESCRIPTION: SEQ ID NO:4:

TTVTAVTTHT GAACVTAATT                                                            20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i x ) FEATURE:
        ( A ) NAME/KEY: miscdifference
        ( B ) LOCATION: replace(3, "")
        ( D ) OTHER INFORMATION: /note="This position is G or A."

( i x ) FEATURE:
        ( A ) NAME/KEY: miscdifference
        ( B ) LOCATION: replace(6, "")
        ( D ) OTHER INFORMATION: /note="This position is A or G."

( i x ) FEATURE:
        ( A ) NAME/KEY: miscdifference
        ( B ) LOCATION: replace(9, "")
        ( D ) OTHER INFORMATION: /note="This position is T or C."

( i x ) FEATURE:
        ( A ) NAME/KEY: miscdifference
        ( B ) LOCATION: replace(15, "")

(D) OTHER INFORMATION: /note="This position is G or A."

(xi) SEQUENCE DESCRIPTION: SEQ ID NO:5:

TTDTADTTHT GGACDTAATT  20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: miscdifference
        (B) LOCATION: replace(3, "")
        (D) OTHER INFORMATION: /note="This position is G or A."

(ix) FEATURE:
        (A) NAME/KEY: miscdifference
        (B) LOCATION: replace(6, "")
        (D) OTHER INFORMATION: /note="This position is A or G."

(ix) FEATURE:
        (A) NAME/KEY: miscdifference
        (B) LOCATION: replace(9, "")
        (D) OTHER INFORMATION: /note="This position is T or C."

(ix) FEATURE:
        (A) NAME/KEY: miscdifference
        (B) LOCATION: replace(15, "")
        (D) OTHER INFORMATION: /note="This position is G or A."

(xi) SEQUENCE DESCRIPTION: SEQ ID NO:6:

TTDTADTTBT GCACDTAATT  20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: miscdifference
        (B) LOCATION: replace(3, "")
        (D) OTHER INFORMATION: /note="This position is G or A."

(ix) FEATURE:
        (A) NAME/KEY: miscdifference
        (B) LOCATION: replace(6, "")
        (D) OTHER INFORMATION: /note="This position is A or G."

(ix) FEATURE:
        (A) NAME/KEY: miscdifference
        (B) LOCATION: replace(9, "")
        (D) OTHER INFORMATION: /note="This position is T or C."

(ix) FEATURE:
        (A) NAME/KEY: miscdifference
        (B) LOCATION: replace(15, "")
        (D) OTHER INFORMATION: /note="This position is G or A."

(xi) SEQUENCE DESCRIPTION: SEQ ID NO:7:

TTDTADTTHT GAACVTAGTT  20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:

(A) NAME/KEY: miscdifference
(B) LOCATION: replace(3, "")
(D) OTHER INFORMATION: /note="This position is G or A."

(ix) FEATURE:
(A) NAME/KEY: miscdifference
(B) LOCATION: replace(6, "")
(D) OTHER INFORMATION: /note="This position is A or G."

(ix) FEATURE:
(A) NAME/KEY: miscdifference
(B) LOCATION: replace(9, "")
(D) OTHER INFORMATION: /note="This position is T or C."

(ix) FEATURE:
(A) NAME/KEY: miscdifference
(B) LOCATION: replace(15, "")
(D) OTHER INFORMATION: /note="This position is G or A."

(xi) SEQUENCE DESCRIPTION: SEQ ID NO:8:

TTDTADTTHT GGACDTAGTT                    20

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (ix) FEATURE:
(A) NAME/KEY: miscdifference
(B) LOCATION: replace(3, "")
(D) OTHER INFORMATION: /note="This position is G or A."

(ix) FEATURE:
(A) NAME/KEY: miscdifference
(B) LOCATION: replace(6, "")
(D) OTHER INFORMATION: /note="This position is A or G."

(ix) FEATURE:
(A) NAME/KEY: miscdifference
(B) LOCATION: replace(9, "")
(D) OTHER INFORMATION: /note="This position is T or C."

(ix) FEATURE:
(A) NAME/KEY: miscdifference
(B) LOCATION: replace(15, "")
(D) OTHER INFORMATION: /note="This position is G or A."

(xi) SEQUENCE DESCRIPTION: SEQ ID NO:9:

TTDTADTTHT GCACDTAGTT                    20

(2) INFORMATION FOR SEQ ID NO:10:

(i) SEQUENCE CHARACTERISTICS:
(A) LENGTH: 14 amino acids
(B) TYPE: amino acid
(C) STRANDEDNESS: single
(D) TOPOLOGY: linear (ix) FEATURE:
(A) NAME/KEY: Modified-site
(B) LOCATION: 9
(D) OTHER INFORMATION: /note="The identity of X at this position could not be determined."

(xi) SEQUENCE DESCRIPTION: SEQ ID NO:10:

Tyr Tyr Ile Val Glu Asp Tyr Gly Xaa Tyr Asn Pro Cys Ser
1               5                   10

(2) INFORMATION FOR SEQ ID NO:11:

(i) SEQUENCE CHARACTERISTICS:
(A) LENGTH: 14 amino acids
(B) TYPE: amino acid (C) STRANDEDNESS: single
(D) TOPOLOGY: linear (ix) FEATURE:
(A) NAME/KEY: Modified-site
(B) LOCATION: 10
(D) OTHER INFORMATION: /note="This position is either Tyr or undetermined."

(xi) SEQUENCE DESCRIPTION: SEQ ID NO:11:

Tyr Tyr Ile Val Glu Asp Tyr Gly Ser Xaa Asn Pro Cys Ser
1               5                   10

(2) INFORMATION FOR SEQ ID NO:12:

(i) SEQUENCE CHARACTERISTICS:
(A) LENGTH: 20 base pairs
(B) TYPE: nucleic acid
(C) STRANDEDNESS: single
(D) TOPOLOGY: linear (ix) FEATURE:
(A) NAME/KEY: miscdifference
(B) LOCATION: replace(3, "")
(D) OTHER INFORMATION: /note="This position is A or G."

(ix) FEATURE:
(A) NAME/KEY: miscdifference
(B) LOCATION: replace(6, "")
(D) OTHER INFORMATION: /note="This position is T or C."

(ix) FEATURE:
(A) NAME/KEY: miscdifference
(B) LOCATION: replace(15, "")
(D) OTHER INFORMATION: /note="This position is A or G."

(ix) FEATURE:
(A) NAME/KEY: miscdifference
(B) LOCATION: replace(18, "")
(D) OTHER INFORMATION: /note="This position is A or G."

(xi) SEQUENCE DESCRIPTION: SEQ ID NO:12:

TADTCHTCNA CDATDTADTA                                          20

(2) INFORMATION FOR SEQ ID NO:13:

(i) SEQUENCE CHARACTERISTICS:
(A) LENGTH: 13 base pairs
(B) TYPE: nucleic acid
(C) STRANDEDNESS: single
(D) TOPOLOGY: linear (xi) SEQUENCE DESCRIPTION: SEQ ID NO:13:

GTCCATTTAG CCA                                                 13

(2) INFORMATION FOR SEQ ID NO:14:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:14:

AATTCAAGCT TG                                                  12

(2) INFORMATION FOR SEQ ID NO:15:

(i) SEQUENCE CHARACTERISTICS:
(A) LENGTH: 12 base pairs
(B) TYPE: nucleic acid
(C) STRANDEDNESS: single
(D) TOPOLOGY: linear ( x i ) SEQUENCE DESCRIPTION: SEQ ID NO:15:

AATTCAAGCT TG                                                                                          12

( 2 ) INFORMATION FOR SEQ ID NO:16:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GACAATGGCT ACACCAGCAC CGCAACGGAC ATTGTTTGGC CC                                                          42

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AAGCAGCCAT TGCCCGAAGC CGAT                                                                             24

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

CTCTGCAGGA ATTCAAGCTA G                                                                                21

( 2 ) INFORMATION FOR SEQ ID NO:19:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

GTAGTTGATA CCGGCACTTG CCAACCCTGT GCAGAC                                                                 36

( 2 ) INFORMATION FOR SEQ ID NO:20:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GTCTGCACAG GGTTGGCAAG TGCCGGTATC AACTAC                                                                 36

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CCGGGATCCG ATCATCACAC C                                                                                21

(2) INFORMATION FOR SEQ ID NO:22:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:22:

AGCCGCAGTG ACCTTCATTG CTGAGGTGTA ATGATG   36

(2) INFORMATION FOR SEQ ID NO:23:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:23:

CATCATTACA CCTCAGCAAT GAAGGTCACT GCGGCT   36

CLONING AND EXPRESSION OF XYLANASE GENES FROM FUNGAL ORIGIN

The present invention relates to the field of molecular biology. In particular, the present invention relates to the cloning and overexpression of a fungal DNA sequence encoding a protein having the activity of a xylanase. The present invention also provides methods for the production and use of a single xylanase which is obtainable in a form which is free of other xylanases, and indeed from other enzymes in general.

BACKGROUND OF THE INVENTION

The composition of a plant cell wall is complex and variable. Polysaccharides are mainly found in the form of long chains of cellulose (the main structural component of the plant cell wall), hemicellulose (comprising various β-xylan chains) and pectin. The occurrence, distribution and structural features of plant cell wall polysaccharides are determined by (1) plant species; (2) variety; (3) tissue type, (4) growth conditions; (5) ageing and (6) processing of plant material prior to feeding.

Basic differences exist between monocotyledons (e.g. cereals and grasses) and dicotyledons (e.g. clover, rapeseed and soybean) and between the seed and vegetative parts of the plant (Chesson, 1987; Carré and Brillouet, 1986). Monocotyledons are characterized by the presence of an arabinoxylan complex as the major hemicellulose backbone. The main structure of hemicellulose in dicotyledons is a xyloglucan complex. Moreover, higher pectin concentrations are found in dicotyledons than in monocotyledons. Seeds are generally very high in pectic substances but relatively low in cellulosic material.

A cross-sectional diagram of a plant cell is depicted in FIG. 1. Three more or less interacting polysaccharide structures can be distinguished in the cell wall:

(1) The middle lamella forms the exterior cell wall. It also serves as the point of attachment for the individual cells to one another within the plant tissue matrix. The middle lamella consists primarily of calcium salts of highly esterified pectins;

(2) The primary wall is situated just inside the middle lamella. It is a well-organized structure of cellulose microfibrils embedded in an amorphous matrix of pectin, hemicellulose, phenolic esters and proteins;

(3) The secondary wall is formed as the plant matures. During the plant's growth and ageing phase, cellulose microfibrils, hemicellulose and lignin are deposited.

The primary cell wall of mature, metabolically active plant cells (e.g. mesophyll and epidermis) is more susceptible to enzymatic hydrolysis than the secondary cell wall, which by this stage, has become highly lignified.

There is a high degree of interaction between cellulose, hemicellulose and pectin in the cell wall. The enzymatic degradation of these rather intensively crosslinked polysaccharide structures is not a simple process. At least five different enzymes are needed to completely break down an arabinoxylan, for example. The endo-cleavage is effected by the use of an endo-$\beta(1\rightarrow4)$-D-xylanase-Exo-$(1\rightarrow4)$-D-xylanase liberates xylose units at the non-reducing end of the polysaccharide. Three other enzymes (α-glucuronidase, L-arabinofuranosidase and acetyl esterase) are used to attack substituents on the xylan backbone. The choice of the specific enzymes is of course dependent on the specific hemicellulose to be degraded (McCleary and Matheson, 1986).

For certain applications, however, complete degradation of the entire hemicellulose into monomers is not necessary or is not desirable. In the liquefaction of arabinoxylan, for example, one needs simply to cleave the main xylan backbone into shorter units. This may be achieved by the action of an endo-xylanase, which ultimately results in a mixture of xylose monomer units and oligomers such as xylobiose and xylotriose. These shorter subunits are then sufficiently soluble for the desired use.

Filamentous fungi are widely known for their capacity to secrete large amounts of a variety of hydrolytic enzymes such as α-amylases, proteases and amyloglucosidases and various plant cell wall degrading enzymes such as cellulases, hemicellulases, and pectinases. Among these, multiple xylan-degrading enzymes have been recognized, which have been shown to possess a variety of biochemical and physical properties. This heterogeneity in xylanase function allows for the selection of a xylanase of interest which is best suited for a desired application (see Wong et al. (1988), Woodward (1984) and Dekker and Richards (1977)).

Multiple xylanases of various molecular weights are known to be produced by micro-organisms such as *Aspergillus niger, Clostridium thermocellum, Trichoderma reesei, Penicillium janthinellum,* as well as species of Bacillus and Streptomyces.

On the contrary, in yeast no xylanase multiplicity has been observed. In three yeast genera, Trichosporon, Cryptococcus and Aureobasidium, only a single xylanase could be detected.

In nature, microbial xylanases are always produced together with other enzymes having polysaccharide-degrading activities, such as exo-arabinanase, acetyl esterase and cellulases. For some applications, these enzyme activities are not needed or are unwanted.

It is known that fermentation conditions may be varied to favor the production of an enzyme of interest. It is also known that the cloning of the gene encoding the desired enzyme and overexpressing it in its natural host, or other compatible expression host will specifically enhance the production of the enzyme of interest. This latter method is particularly useful if the enzyme of interest is to be obtained in a form which is free of undesired enzyme activity.

The expression of recombinant bacterial xylanase has been previously described in European Patent Application 121.138. The gene encoding the bacterial xylanase was isolated from Bacillus chromosomal DNA and brought to expression in an *E. coli* host. However, *E. coli* expression hosts are, in some instances, considered to be unsafe for the production of proteins by recombinant DNA methods due to their production of unacceptable by-products such as toxins.

Since bacterial genes contain no introns, one is confronted with few problems in cloning and expressing such genes in prokaryotic hosts. On the other hand, the expression of eukaryotic genes is not always so straightforward. It is well known that genes isolated from eukaryotic strains contain introns. This inherently introduces complications in the cloning and expression of these genes, should a prokaryotic host be preferred.

Furthermore, certain differences exist, in general, between the physical characteristics of xylanases of fungal origin and those from bacteria. In general, fungal xylanases have a pH optimum in the range of between pH 3.5–5.5 as compared to bacterial xylanases which generally have a pH optimum in the range of pH 5.0–7.0. Fungal xylanases also generally have a broader pH stability range (pH 3–10) than do their bacterial counterparts (pH 5.0–7.5). Fungal xylanases generally have a temperature optimum of about 50° C. Bacterial xylanases generally have a temperature optimum between 50° C. and 70° C. For a further discussion of the physical characteristics of xylanases see Wong et al. (1988), Woodward (1984) and Dekker and Richards (1977).

Thus, it is clear that bacterial xylanases are less suitable for use in, for example, processes requiring lower pH conditions. In other instances, bacterial xylanases are too thermostable for certain applications such as the lagering of beer (see European Patent No. 227,159).

Accordingly, it would be of great importance to obtain genes encoding xylan-degrading enzymes of fungal origin which may be brought to expression in other, high-producing microbial expression hosts.

SUMMARY OF THE INVENTION

The present invention provides purified and isolated DNA sequences of fungal origin, which encode proteins having xylan-degrading activity. These DNA sequences include the xylanase encoding sequence and preferably the adjacent 5' and 3' regulatory sequences as well.

It is also an object of the present invention to provide constructs for the microbial overexpression of the xylanase-encoding sequences using either their native regulatory sequences or, in an alternative embodiment, the xylanase-encoding sequence operably linked to selected regulatory regions such as promoter, secretion leader and terminator signals which are capable of directing the overexpression of the xylanase protein in a suitable expression host.

It is a further object of the present invention to provide microbial expression hosts, transformed with the expression constructs of the present invention, which are capable of the overexpression and, if desired, the secretion of a xylanase of fungal origin.

It is yet a further object of the present invention to provide methods for the production of a xylanase of interest which may, in turn, advantageously be used in an industrial process. Typically, such an industrial process requires xylanase activity at a lower pH than that at which xylanases of bacterial origin optimally function.

BRIEF DESCRIPTION OF THE FIGURES

FIG. 3: (SEQ ID NO:4, SEQ ID NO:5, SEQ ID NO:6, SEQ ID NO:7, SEQ ID NO:8, SEQ ID NO:9 and SEQ ID NO:10) Oligonucleotide probes AB8-01–AB806, designed from the N-terminal amino acid sequence of the *Aspergillus tubigensis* XYL A protein. (Formula 1).

FIG. 4: (SEQ ID NO:11, SEQ ID NO:12 and SEQ ID NO:13) Oligonucleotide probe AB1255, designed from the N-terminal amino acid sequence of an internal 19 kDa fragment of the *Aspergillus tubigensis* XYL A protein, digested with the *S. aureus* V8 endopeptidase (Formula 2).

FIG. 8: (SEQ ID NO:1, SEQ ID NO:2 and SEQ ID NO:3) Nucleotide sequence of the *Aspergillus tubigensis* xln A gene. The positions of the intron and the pro-peptide are putative.

FIG. 10: SDS-polyacrylamide gel electrophoresis showing the expression of the XYL A protein in *A. niger* CBS 513.88 (A) and *A. niger* N593 (B).

FIG. 11: Native gradient PAGE exhibiting the XYL A protein expressed by *A. niger* CBS 513.88 transformants numbers 10, 29 and 1.1, stained with CBB (A) and with an RBB-xylan overlay (B).

FIG. 19: Partial restriction map of the 6.5 kb BglII/-SalI fragment from *T. reesei* cloned into pEMBL18 (pIM030). The hatched box represents the hybridizing fragment within the insert.

FIG. 20: Partial restriction map of the 7.5 kb BamHI/BglII fragment from *T. reesei* cloned in PUC9 (pIM041). The hatched box represents the hybridizing fragment within the insert.

DETAILED DESCRIPTION OF THE INVENTION

Figure 1:
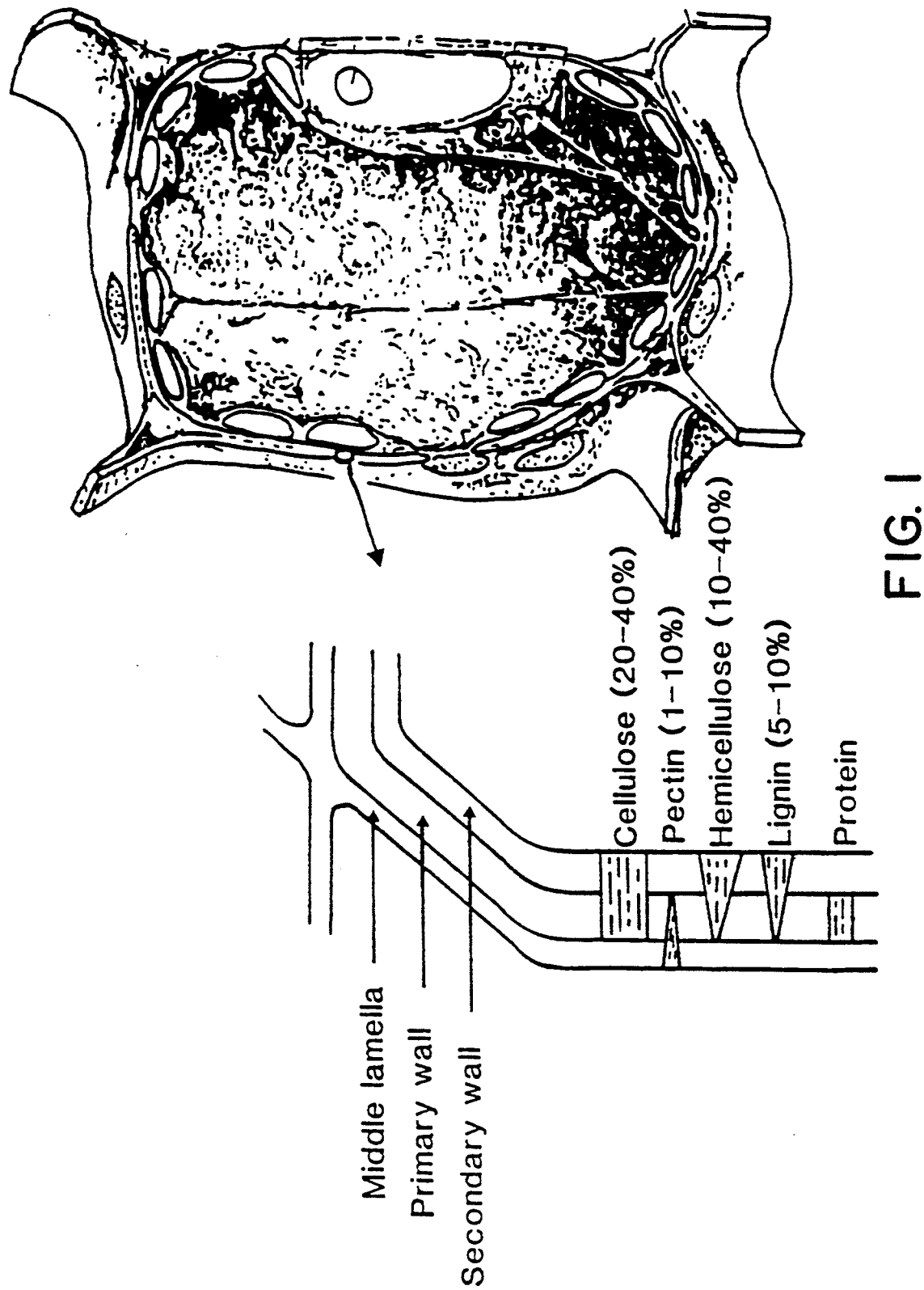
FIG. 1: A cross-sectional diagram of a plant cell.

The present invention describes purified and isolated DNA sequences of fungal origin which encode xylanases and genetic variants thereof. The DNA sequence preferably includes the xylanase-encoding sequence and adjacent 5' and 3' regulatory sequences. Genetic variants include hybrid DNA sequences containing the xylanase-encoding sequence coupled to regulatory regions, such as promoter, secretion and terminator signals, originating from homologous or heterologous organisms. Genetic variants also include DNA sequences encoding mutant xylanase proteins and degenerate DNA sequences wherein the xylan-degrading activity of the enzyme is retained. The present invention also includes DNA sequences which are capable of hybridizing to the xylanase-encoding DNA sequences and genetic variants thereof, as described above, but which may differ in codon sequence due to the degeneracy of the genetic code or cross-species variation.

The present invention also provides DNA constructs for the expression of a xylanase of interest in a desired expression host. These expression constructs include hybrid DNA sequences containing the xylanase-encoding region operably linked to regulatory regions, such as promoter, secretion and terminator signals originating from homologous or heterologous organisms, these regulatory regions being capable of directing the overexpression of the enzyme encoded by the xylanase-encoding DNA sequence in an appropriate host. Preferably, the expression construct will be integrated into the genome of the selected expression host.

The present invention further provides vectors, preferably plasmids, for the cloning and/or transformation of microbial hosts via the introduction into the microbial host of the DNA constructs for the expression of the xylanase of interest.

In addition, the present invention concerns homologous or heterologous hosts transformed by DNA constructs described above. Microbial expression hosts may be selected from bacteria, yeasts or fungi.

Within the context of the present invention, the term "homologous" is understood to intend all that which is native to the DNA sequence encoding the xylanase of interest, including its regulatory regions. A homologous host is defined as the species from which such DNA sequence may be isolated.

The term "heterologous" is thus defined as all that which is not native to the DNA sequence encoding the xylanase of interest itself, including regulatory regions. A "heterologous" host is defined as any microbial species other than that from which the xylanase-encoding gene has been isolated.

Within the scope of the present invention, a xylanase of interest is understood to include any xylan-degrading enzyme which is naturally produced by a filamentous fungus. Xylanases of particular interest are those which are naturally produced by filamentous fungi of the genera *Aspergillus, Disporotrichum, Penicillium, Neurospora, Fusarium* and *Trichoderma*. Especially preferred xylanases are those originating from *Aspergillus niger, Aspergillus awamori, Aspergillus aculeatus, Aspergillus tubigensis, Disporotrichum dimorphosporum* and *Trichoderma reesei*. Most preferred are the xylanases originating from *Aspergillus tubigensis* and *Trichoderma reesei*.

An endo-xylanase of interest may be identified via assay methods not critical to the present invention, such as a spot test assay. According to this method, a filtrate obtained from the culturing of a microorganism induced (e.g. with oat spelt xylan) to produce an endo-xylanase may be tested for the presence of endo-xylanase activity. Drops of the elution fractions are placed individually onto an agar film containing a citrate-phosphate buffer (see Example 1.1, below) and oat spelt xylan. The film is then incubated. If endo-xylanase activity is present, the location of the individual drops on the agar film are visibly clear.

Once a xylanase of interest has been identified, the DNA sequence encoding such xylanase may be obtained from the filamentous fungus which naturally produces it by culturing the fungus in a xylan-containing medium, isolating the desired xylanase using known methods such as column chromatography (e.g. HPLC—see FIG. 2) and determining at least a portion of the amino acid sequence of the purified protein.

DNA probes may thereafter be designed by synthesizing oligonucleotide sequences based on the partial amino acid sequence. Amino acid sequences may be determined from the N-terminus of the complete protein and/or from the N-termini of internal peptide fragments obtained via proteolytic or chemical digestion of the complete protein. Once obtained, the DNA probe(s) are then used to screen a genomic or cDNA library.

If this method is unsuccessful, the genomic library may be differentially screened with cDNA probes obtained from mRNA from non-induced and induced cells. Induced mRNA is prepared from cells grown on media containing xylan as a carbon source, while non-induced mRNA must be isolated from cells grown on a carbon source other than xylan, e.g. glucose. Among the clones which only hybridize with the induced cDNA probe, a clone containing the desired xylanase gene may be recovered. Alternatively, a xylanase gene may be identified by cross-hybridization with a related xylanase sequence (see Example 7, below).

A genomic library may be prepared by partially digesting the fungal chromosomal DNA with a suitable restriction enzyme, e.g. Sau3A, and cloning the resulting fragments in a suitable plasmid or lambda phage vector, e.g. lambda EMBL 3. Subsequently, after plating of a sufficient amount of colonies or plaques, the genomic or cDNA library may be screened with a suitable DNA probe.

Alternatively, a cDNA library may be prepared by cloning cDNA, synthesized from mRNA isolated from fungal cells induced for the synthesis of xylanase, into an appropriate phage vector, e.g. lambda gt 10 or lambda gt 11. The cDNA library may then be screened with a DNA probe, or alternatively using immunological means or via a plate assay.

In a preferred embodiment of the present invention, oligonucleotide probes are designed from the N-terminal amino acid sequence (see FIG. 3, formula 1) of a xylanase having an apparent molecular weight of 25 kDa purified from an *Aspergillus tubigensis* culture filtrate and/or from the amino acid sequence of an internal peptide fragment (see FIG. 4, formula 2) obtained by digestion of the xylanase with *Staphylococcus aureus* endoprotease V8. The oligonucleotide mixtures as depicted in FIGS. 3 and 4 are complementary to the corresponding deduced xylanase mRNA. Four positive phage clones were obtained from the screening of a lambda EMBL 3 library, prepared from partially SaU3A digested DNA isolated from *Aspergillus niger* DS16813, with the N-terminal oligo mixture AB 800 (a mixture of equal amounts of AB801 through AB806, see FIG. 3). *Aspergillus niger* DS16813, later reclassified as more likely belonging to the species *Aspergillus tubigensis* (Kusters-van Someren et al. (1991)), was deposited at the Centraal Bureau voor Schimmelcultures, Baarn, The Netherlands on Jul. 20, 1990 and was assigned the designation CBS 323.90.

DNA isolated from the four phage clones hybridized with the N-terminal oligo mixture as well as with the oligo mixture derived from the amino acid sequence of the internal fragment (see FIG. 4). Restriction enzyme analysis revealed that all four clones contained DNA from the same genomic region of *A. tubigensis*.

A region of approximately 2.1 kb which hybridizes with both oligo mixtures has been sequenced. The nucleotide sequence, as depicted in FIG. 8, comprises a xylanase coding sequence of 681 bp (which is interrupted by one small intron of 49 bp from position 1179 to 1230), as well as sequences of 949 and 423 nucleotides of the 5' and 3' flanking regions, respectively.

Variants among the purified xylanase proteins have also been discovered. It has been determined that the corresponding xylanases have three different N-termini, possibly as a result of fermentation conditions. Approximately one-third of these xylanases have serine as the N-terminal amino acid (FIG. 8, position 1), another approximately one-third have alanine as the N-terminal amino acid (FIG. 8, position 2) and the remaining proteins have glycine as the N-terminal amino acid (FIG. 8, position 3).

The availability of a DNA sequence encoding a xylanase protein enables the construction of mutant xylanases by site-directed mutagenesis. If the tertiary structure of the xylanase is known, and its catalytic and substrate binding domains are localized, amino acids may be selected for mutagenesis (for example with the aid of computer modelling) which most likely affect catalytic and/or substrate binding functions. If the tertiary structure of the protein is not available, random mutants may be either generated along with the entire coding sequence, or the tertiary structure of the protein may be predicted by comparison with similar known xylanases isolated from another microorganism.

To facilitate the insertion of the DNA fragment containing the xylanase-encoding sequence into expression constructs comprising one or more heterologous regulatory regions, the polymerase chain reaction (PCR) (Ehrlich, H. A. (editor), 1989) may be used for introduction of appropriate restriction enzyme sites in the 5' and 3' ends of the xylanase coding sequence. The choice of restriction sites depends on the DNA sequence of the expression vector, i.e. the presence of other restriction sites within the DNA molecule.

To obtain overexpression of the xylanase protein in the original (homologous) production species, or alternatively in another fungal strain, a 6.9 kb SalI fragment (see FIG. 5) comprising the complete gene with its 5' and 3' regulatory regions, or alternatively, the complete gene fused to the regulatory regions of other genes, is introduced into the selected expression host to increase the copy number of the gene and, consequently, protein expression.

If a heterologous expression host is preferred, and a yeast or a bacterial strain is selected, an uninterrupted (intronless) DNA sequence is used for the construction of a heterologous expression vector in order to avoid the possibility that splice signals residing on the genomic fragment are not recognized by the heterologous host. This uninterrupted DNA sequence may be obtained from a cDNA library constructed from mRNA isolated from cells, induced for the synthesis of xylanases. This library may be screened with an oligonucleotide or cDNA probe obtained as described before. Alternatively, an uninterrupted DNA sequence may be obtained by applying a polymerase chain reaction using appropriate 5' and 3' oligonucleotides on the first strand cDNA synthesized from the RNA of xylan-induced cells.

Within the context of the present invention, overexpression is defined as the expression of the xylanase of interest at levels above that which are ordinarily encountered in the homologous wild-type organism. In the same context, overexpression also intends the expression of the xylanase of interest in a heterologous organism which does not normally produce such xylanase except for the introduction of the DNA sequence encoding the xylanase of interest into the heterologous expression host. Progeny of these expression hosts are, of course, also to be understood to be embraced by the present invention.

Overexpression of the xylanase of interest may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the xylanase of interest.

Aside from the xylanase of interest's native promoter, other promoters may be used to direct its expression. The promoter may be selected for its efficiency in directing the expression of the xylanase of interest in the desired expression host.

In another embodiment, a constitutive promoter may be selected to direct the expression of the desired xylanase, relatively free from other xylanases. Such an expression construct is furthermore advantageous since it circumvents the need to culture the expression hosts on a medium containing solid xylans as an inducing substrate.

Examples of strong constitutive and/or inducible promoters which are preferred for use in fungal expression hosts are the ATP-synthetase, subunit 9 (oliC), triose phosphate isomerase (tpi), alcohol dehydrogenase (adhA), amylase (amy), amyloglucosidase (AG), acetamidase (amdS) and glyceraldehyde-3-phosphate dehydrogenase (gpd) promoters.

Examples of strong yeast promoters are the alcohol dehydrogenase, lactase, 3-phosphoglycerate kinase and triosephosphate isomerase promoters.

Examples of strong bacterial promoters are the α-amylase and Spo2 promoters as well as promoters from extracellular protease genes.

Hybrid promoters may also advantageously be used to improve inducible regulation of the expression construct.

Preferred promoters according to the present invention are those originating from the amyloglucosidase (AG) gene and native xylanase promoters.

It is often desirable for the xylanase of interest to be secreted from the expression host into the culture medium from where the xylanase may be more easily recovered.

According to the present invention, the xylanase of interest's native secretion leader sequence may be used to effect the secretion of the expressed xylanase.

However, an increase in the expression of the xylanase sometimes results in the production of the protein in levels beyond that which the expression host is capable of processing and secreting, creating a build-up of protein product within the cell due to a bottleneck in the transport of the protein through the cell wall. Accordingly, the present invention also provides heterologous leader sequences to provide for the most efficient secretion of the xylanase from the chosen expression host.

According to the present invention, the secretion leader may be selected on the basis of the desired expression host. A heterologous secretion leader may be chosen which is homologous to the other regulatory regions of the expression construct. For example, the leader of the highly secreted amyloglucosidase protein may be used in combination with the amyloglucosidase promoter itself, as well as in combination with other promoters. Hybrid signal sequences may also advantageously be used within the context of the present invention.

Examples of preferred heterologous secretion leader sequences are those originating from the amyloglucosidase gene (fungi), the α-factor gene (yeasts) or the α-amylase gene (Bacillus).

Most preferred secretion leader sequences according to the present invention are the those originating from the amyloglucosidase (AG) gene and the native xylanase leader sequence.

In general, terminators are not considered to be critical elements for the overexpression of genes. If desired, a terminator may be selected from the same genes as the promoters, or alternatively, the homologous terminator may be employed.

In addition to the genomic fragment mentioned above, the transforming DNA may contain a selection marker to discriminate cells which have incorporated the desired gene from the bulk of untransformed cells. This selection marker, provided with the appropriate 5' and 3' regulatory sequences, may reside on the same DNA molecule containing the desired gene or be present on a separate molecule. In the latter case, a co-transformation must be performed. The ratio of the expression vector/selection vector must be adjusted in such a manner that a high percentage of the selected transformants also have incorporated the vector containing the expression construct of the xylanase of interest.

The most suitable selection systems for industrial micro-organisms are those formed by the group of selection markers which do not require a mutation in the host organism. Examples of fungal selection markers are the genes for acetamidase (amdS), ATP synthetase, subunit 9 (oliC) and benomyl resistance (benA). Exemplary of non-fungal selection markers are the G418 resistance gene (yeast), the ampicillin resistance gene (*E. coli*) and the neomycin resistance gene (Bacillus).

Once the desired expression construct has been assembled, it is transformed into a suitable cloning host such as *E. coli* to propagate the construct. Afterwards, the expression construct is introduced into a suitable expression host wherein the expression construct is preferably integrated into the genome. Certain hosts such as Bacillus species may be used as both cloning and expression hosts, thus avoiding an extra transformation step.

According to the present invention, a variety of expression hosts may be used to overexpress the xylanase of interest. In one embodiment, a homologous expression host may be used. This involves the introduction of the desired expression construct back into the strain from which the xylanase encoding DNA sequence was isolated either in increased gene copy numbers, or under the control of heterologous regulatory regions as described above, or both.

In another embodiment, a xylanase of interest may be overexpressed by introducing and expressing the DNA construct encoding the xylanase of interest under the control of the appropriate regulatory regions in heterologous hosts such as bacteria, yeasts or fungi. For that purpose, the DNA sequence encoding the xylanase of interest is preferably expressed under the control of promoter and terminator sequences originating from the heterologous host. In addition, it may be necessary to replace the native secretion leader sequence of the xylanase of interest with a leader sequence homologous to the expression host in order to achieve the most efficient expression and secretion of the product.

Factors such as the size (molecular weight), the possible need for glycosylation or the desirability of the extracellular secretion of the xylanase of interest play an important role in the selection of the expression host.

The gram-negative bacterium *E. coli* is widely used as a host for heterologous gene expression, but mostly accumulates large amounts of heterologous protein inside the cell. Subsequent purification of the desired protein from the bulk of *E. coli* intracellular proteins can sometimes be difficult.

In contrast to *E. coli*, bacteria from the genus Bacillus are very suitable as heterologous hosts because of their capability to secrete proteins into the culture medium.

Alternatively, a heterologous host selected from the group of yeasts or fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a fungal host organism should be selected.

A heterologous host may also be chosen to express the xylanase of interest substantially free from other polysaccharide-degrading enzymes by choosing a host which does not normally produce such enzymes such as *Kluyveromyces lactis*.

Examples of preferred expression hosts within the scope of the present invention are fungi such as Aspegillus species (described in EP 184,438 and EP 284.603) and Trichoderma species, bacteria such as Bacillus species (described in EP 134.048) and yeasts such as Kluyveromyces species (described in EP 96,430 and EP 301,670) and Sacchromyces species.

Particularly preferred expression hosts may be selected from *Aspergillus niger, Aspergillus awamori, Aspergillus aculeatus, Aspergillus oryzae, Aspergillus tubigensis, Trichoderma reesei, Bacillus subtills, Bacillus licheniformis, Kluyveromyces lactis* and *Saccharomyces cerevisiae.*

The overexpression of the xylanase of interest is effected by the culturing of the expression hosts, which have been transformed with the xylanase expression construct, in a conventional nutrient fermentation medium.

The fermentation medium consists of an ordinary culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). optionally, an inducer (e.g. oat spelt xylan) may be included.

The selection of the appropriate medium may be based on the choice of expression hosts and/or based on the regulatory requirements of the expression construct. Such media are well-known to those skilled in the art. The medium may, if desired, contain additional components favoring the transformed expression hosts over other potentially contaminating microorganisms.

The fermentation is performed over a period of 0.5–20 days in a batch or fed-batch process at a temperature in the range of between 0° and 45° C. and a pH between 2 and 10. Preferred fermentation conditions are a temperature in the range of between 20° and 37° C. and a pH between 3 and 9. The appropriate conditions are selected based on the choice of the expression host.

After fermentation, the cells are removed from the fermentation broth by means of centrifugation or filtration. After removal of the cells, The xylanase of interest may then be recovered and, if desired, purified and isolated by conventional means.

The product is stably formulated either in liquid or dry form. For certain applications, immobilization of the enzyme on a solid matrix may be preferred.

Xylanases of interest, produced by means of the present invention, may be applied either alone, or together with other selected enzymes in a variety of processes requiring the action of a xylan-degrading enzyme. Moreover, the fungal xylanases of the present invention, which generally have lower pH optima than xylanases of bacterial origin, are particularly well suited for use in industrial processes which are performed at low pH.

In accordance with the present invention, it has been found that the xylanases produced via the present invention may be used in the baking of breads. The incorporation of small amounts of xylanase to the flour imparts favorable characteristics to the dough and thus to the bread itself such as increased loaf volume and better textural characteristics such as break and shred quality and crumb quality.

Xylanases may also be added to animal feed compositions which are rich in arabinoxylans and glucoxylans. When added to feeds (including silage) for monogastric animals (e.g. poultry or swine) which contain cereals such as barley, wheat, maize, rye or oats or cereal by-products such as wheat bran or maize bran, the enzyme significantly improves the break-down of plant cell walls which leads to better utilization of the plant nutrients by the animal. As a consequence, growth rate and/or feed conversion are improved. Moreover, xylanases may be used to the reduce the viscosity of feeds containing xylans.

Xylanase may be added beforehand to the feed or silage if pre-soaking or wet diets are preferred. More advantageously, however, the xylanases produced via the present invention when added to feed continue to hydrolyze xylans in the feed in vivo. Fungal xylanases, which generally have lower pH optima, are capable of releasing important nutrients in such acidic environments as the stomach of the animal ingesting such xylanase-supplemented feed.

The xylanases produced via the present invention are also effective in improving filtration and removing dissolved organic substances from the broth in processes wherein apple distillery waste is bioconverted into microbial biomass. Xylanases originating from filamentous fungi may be advantageously used in this process.

Also according to the present invention, glucose syrups having improved filterability and/or lower viscosity are produced from impure cereal starch by subjecting the impure starch first to the action of an α-amylase, then to fungal xylanases produced via the present invention and finally to a hydrolysis. Similarly, the xylanases of the present invention may be used in beer brewing to improve the filterability of the wort.

Xylanases may also be used to remove lignins from kraft pulp and thus facilitate bleaching by reducing the amount of chlorine needed in the preparation of paper products.

In addition, the xylanases produced via the present invention may be used in other processes such as to increase yield in the preparation of fruit or vegetable juices, the enzymatic hydrolysis of sugar beet pulp, the resulting hydrolyzed fraction being capable of use in microorganism culture medium; of agricultural residues such as corn cobs, wheat-straw and ground nutshell; and of certain recyclable materials such as waste paper.

The following examples are provided so as to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, pH, etc.) but some experimental errors and deviation should be accounted for. Unless indicated otherwise, temperature is in degrees Celsius and pressure is at or near atmospheric.

EXAMPLE 1

Purification and Characterization of *Aspergillus tubigensis* Endo-xylanase XYL A Example 1.1

Purification of *Aspergillus tubigensis* Endo-xylanase XYL A

A culture filtrate was obtained by the culturing of *Aspergillus niger* DS16813 (CBS 323.90—later reclassified as more likely belonging to the species *A. tubigensis;* Kusters-van Someren et al. (1991)) in a medium containing (per liter): 30 g oat spelt xylan (Sigma); 7.5 g NH$_4$NO$_3$, 0.5 g KCl, 0.5 g MgSO$_4$, 15 g KH$_2$PO$_4$, and 0.5 g yeast extract (pH 6.0). The culture filtrate was concentrated to a volume of approximately 35 ml which was then was ultrafiltered on a Diaflo PM 10 filter in a 50 ml Amicon module to remove salts.

The supernatant was then concentrated to a volume of ml and the retentate was washed twice with 25 ml 25 mM Tris-HCl buffer (pH 7.0). After washing, the retentate volume was brought to 25 ml.

This retentate was injected in 1 ml quantities onto a Syn Chropak AX 300 column (dimensions 10×250 mm) and eluted in the following HPLC regime:

| elution rate: | 2 ml/min. | |
|---|---|---|
| elution buffer A: | 25 mM Tris-HCl pH 7.0 | |
| elution buffer B: | 25 mM Tris-HCl pH 7.0 + 1M NaCl | |
| elution gradient: | time | | |
| | (min) | % A | % B |
| | 0 | 99 | 1 |
| | 12 | 97 | 3 |
| | 30 | 80 | 20 |
| | 50 | 50 | 50 |
| | 70 | 0 | 100 |
| | 90 | 0 | 100 |
| | 95 | 99 | 1 |

Figure 2:
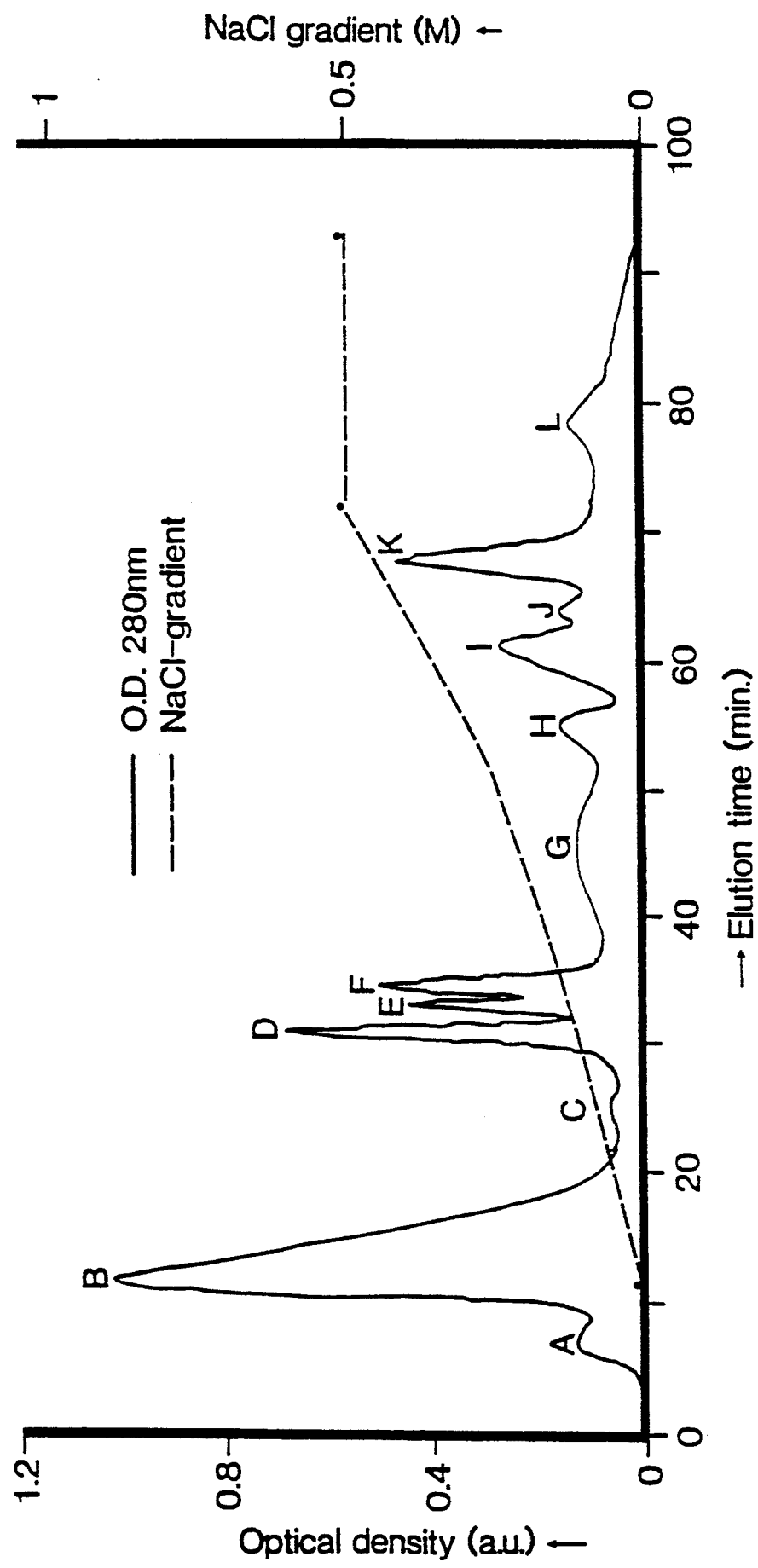
FIG. 2: HPLC elution profile of a culture filtrate obtained from *Aspergillus niger* DS16813 (CBS 323.90). This strain was later reclassified as more likely belonging to the species *Aspergillus tubigensis*.

Fractions of 1 ml each were collected. Detection of the eluted protein was performed by continuous measurement of the UV absorption at 280 nm. The elution profile is shown in FIG. 2.

The fractions were tested for the presence of endoxylanase activity by a spot test. This spot test consists of adding 12 ml citrate-phosphate buffer (prepared by mixing 900 ml 0.2 M Na₂HPO₄ and 125 ml 0.5 M citric acid, followed by an adjustment of the pH of the solution to pH 5.6 using 0.5 M citric acid or 0.2 M Na₂HPO₄) containing 0.5% oat spelt xylan (Sigma) to 180 mg agar (Difco) and heating the mixture to 100° C. to dissolve the agar. After cooling to 60° C., the agar mixture is poured evenly onto Agarose gel-bond film. Drops of the elution fractions are placed individually onto the film and incubated for 30 min. at 30° C. If endoxylanase activity is present, the location of the individual drops on the agar film is clear.

Total xylanase activity in the collected fractions was quantitatively determined by measuring the amount of reducing sugars produced over a predetermined time period in the microassay as described by Leathers et al. (1984), using oat spelt xylan in 50 mM sodium acetate at pH 5.0 as a substrate. Activity units are also as defined by Leathers (supra).

Exo-xylanase activity in the eluted fractions was determined by the method described by Poutanen and Puls (1988), using p-nitro-phenyl-β-D-xylopyranoside (0.3 mM, Sigma) as a substrate at pH 5.0 nd 30° C.

The spot test revealed that the elution fractions corresponding to peaks B, F and K (see FIG. 2) contain endo-xylanase activity. The total xylanase assay showed activity in the elution fractions of peaks B, F, H and K. The elution fractions of peaks B and H were determined to contain exo-xylanase activity.

The elution fractions of peaks F (XYL2 protein) and K (XYL A protein) were further purified by repeated ion exchange chromatography. The endo-xylanases contained therein were characterized by SDS/PAGE (Moonen et al., 1982) and Iso Electric Focusing (3.5<pH<9.5) on LKB equipment according to the manufacturer's instructions. The apparent molecular weight of endo-xylanase F, as determined by SDS-PAGE, was approximately 22 kDa; the apparent molecular weight of endo-xylanase K was approximately 24 kDa. The isoelectric point (IEP) of endo-xylanase F was approximately pH 4.0, while the IEP of endo-xylanase K was determined to be lower than pH 3.5.

Example 1.2

Amino Acid Sequencing of the N-terminus of *Aspergillus tubigensis* Endo-xylanase XYL A Approximately 5 μg of endo-xylanase, purified as described in Example 1.1, was subjected to electrophoresis on a 12% SDS-polyacrylamide gel, followed by electroblotting onto Immobilon-P membrane (Millipore), according to the method described by Matsudaira (1987). The membrane fragment containing the main band having an apparent molecular weight (SDS-PAGE) of 25 kDa is subjected to sequence analysis in a gas-phase sequenator (Euroseguence, Groningen). The following N-terminal sequence has been determined:

```
1               5                      10
Ala—Gly—Ile—Asn—Tyr—Val—Gln—Asn—Tyr—Asn
```
(Figure 3, Formula 1) (SEQ ID NO: 4)

However, roughly equal amounts of two other variants were also discovered wherein either a serine (FIG. 8, position 1) or a glycine (FIG. 8, position 3) were determined to be the N-terminal amino acid.

Example 1.3

Amino Acid Sequence Determination of Endo-proteinase Glu-C Released Peptides of Endo-Xylanase XYL A Approximately 260 μg of endo-xylanase, purified as described in Example 1.1, was dissolved in 110 μl of a solution containing 50 mM ammonium bicarbonate buffer pH 7.5 and 2 mg/ml SDS. After heating the solution for three minutes at 100° C. and cooling to room temperature, endoproteinase Glu-C (Staphylococcus aureus protease V8) was added in an 18-fold molar excess. Protein digestion was performed for 20 minutes at room temperature, after which the reaction mixture was heated for three minutes at 100° C.

Approximately one-fifth of the reaction mixture was subjected to electrophoresis on a 15% SDS-polyacrylamide gel, followed by blotting onto Immobilon-P membrane (Millipore) according to the method described by Matsudaira (1987). Three fragments were observed with a molecular mass of 19, 16 and 4 kDa respectively. The two largest fragments (19 and 16 kDa) were used in gas-phase sequencing (Applied Biosystems model 470A protein sequencer, Eurosequence, Groningen). Membrane fragments containing 2–3 nmol of the particular peptide were washed and subjected to sequence analysis, according to the program described by Amons (1987).

The following N-terminal amino acid sequence has been determined from the 19 kDa fragment:

```
1               5                      10                  14
Tyr—Tyr—Ile—Val—Glu—Asp—Tyr—Gly—X—Tyr—Asn—Pro—Cys—(Ser)
```
(Figure 4, Formula 2) (SEQ ID NO: 11)

The identity of the amino acid at position 9 (X), could not be determined. At position 14, only a trace of Ser is found as indicated by brackets.

The following amino acid sequence has been determined from the N-terminus of the 16 kDa fragment:

```
1               5                      10                  14
Tyr—Tyr—Ile—Val—Glu—Asp—Tyr—Gly—(Ser)—X—Asn—Pro—Cys—Ser
```
(Figure 4, Formula 3) (SEQ ID NO: 12)

The identity of amino acid (X) at position 10 could not be determined. The sequence found for this fragment is almost identical to the sequence of the 19 kDa fragment. Both peptides share the same N-terminal sequence, which is not identical to the N-terminal amino acid sequence determined for the intact protein (Example 1.2, Formula 1). It has been determined that these two internal fragments correspond to the sequence beginning with position 79 as illustrated in FIG. 8.

EXAMPLE 2

Construction of a Genomic Library of *Aspergillus niger* Strain DS16813 (CBS 323.90; Later Reclassified as *A. tubigenss*)

Example 2.1

Isolation of DNA from *Aspergillus niger* DS16813 (CBS 323.90; later reclassified as *A. tubigensis*)

Fungal DNA was isolated via the procedure described by de Graaff et al. (1988). Mycelium, grown overnight in liquid minimal medium (per 1000 ml: 6.0 g $NANO_3$; 1.5 g $KH_2PO_4$; 0.5 g $MgSO_4.7H_2O$; 0.5 g KCl; 1 ml Visniac solution [Visniac and Santer, 1957: 10 g EDTA; 4.4 g $ZnSO_4.7H_2O$; 1.0 g $MnCl_2.4H_2O$; 0.32 g $CoCl_2.6H_2O$; 0.32 g $CuSO_4.5H_2O$; 0.22 g $(NH_4)_6Mo_7O_{24}.4H_2O$; 1.47 g $CaCl_2.2H_2O$; 1.0 g $FeSO_4.7H_2O$; pH 4.0]; pH 6.0) supplemented with 0.2% casamino acids and 0.5% yeast extract, was harvested, washed with cold saline, frozen in liquid nitrogen and stored at $-80°$ C. Nucleic acids were isolated by disrupting 0.5 g frozen mycelium using a microdismembrator (Braun). The mycelial powder obtained was extracted with freshly prepared extraction buffer.

The extraction buffer was prepared as follows: 1 ml tri-isopropylnaphtalene sulfonic acid (TNS) (20 mg/ml) was thoroughly mixed with 1 ml p-aminosalicylic acid (PAS) (120 mg/ml) and 0.5 ml 5×RNB buffer (per 1000 ml: 121.10 g Tris; 73.04 g NaCl; 95.10 g EGTA; adjusted to pH 8.5 with HCl) was added. After the addition of 1.5 ml phenol, the extraction buffer was equilibrated for 10 minutes at 55° C. The warm buffer was then added to the mycelial powder, and the suspension was thoroughly mixed for 1 minute using a vortex mixer. After the addition of 1 ml chloroform, the suspension was remixed for 1 min. After centrifugation at $10^4 \times g$ for 10 min. using a Sorvall high speed centrifuge, the aqueous phase was extracted once more with an equal volume of phenol/chloroform (1:1) and was then extracted twice with chloroform. DNA was isolated from the aqueous phase using the following procedure; the DNA was immediately precipitated with 2 volumes ethanol at room temperature and was subsequently collected by centrifugation using a Sorvall high speed centrifuge at $10^4 \times g$ for 10 min., washed twice by redissolving the DNA in distilled, sterile water and precipitating it again with ethanol. RNA was removed by adding RNase A (20 g µg/ml) to the final solution.

Example 2.2

Partial Digestion of *Aspergillus tubigensis* DNA With Sau3A and Isolation of DNA Fragments After Agarose Gel Electrophoresis DNA (30 µg), isolated from *Aspergillus niger* DS16813 (recently reclassified as *A. tubigensis*) as described in Example 2.1, was partially digested by incubation of the DNA with 0.1 U Sau3A during 30 minutes at 37° C. The resulting fragments were size fractionated by electrophoresis on 0.4% agarose in TAE buffer containing 0.5 µg/ml ethidiumbromide, Fragments of 14 kb to 22 kb in size, compared to fragments of bacteriophage lambda DNA digested with BglII (22.0, 13.3, 9.7, 2.4, 0.65 and 0.44 kb) as size markers, were recovered from the gel by cutting the appropriate region from the gel.

These fragments were recovered from the piece of agarose by electro-elution using ISCO cups. A dialysis membrane was mounted on both the large and the small containers of this cup, the cup was filled with 0.005×TAE (diluted from 50×TAE stock solution (per 1000 ml): 242.0 g Tris; 57.1 ml glacial acetic acid; 100 ml 0.5 M EDTA; adjusted to pH 8.0 with HCl) and the piece of agarose was placed in the large container of the cup. Subsequently, the cup was placed in the electro-elution apparatus, with the large container in the cathode chamber containing TAE and the small container at the anode chamber containing TAE/3 M NaCl. The fragments were electro-eluted at 100 V for a period of 2 hours. Afterwards, the cup was taken from the electro-elution apparatus and the buffer was removed from the large container, while the buffer was removed only from the upper part of the small container. The remaining buffer (200 µl) containing the DNA fragments was dialyzed in the cup against distilled water for a period of 30 minutes. Finally, the DNA was precipitated by the addition of 0.1 volume 3 M NaAc, pH 5.6 and 2 volumes cold ($-20°$ C.) ethanol. The DNA was collected by centrifugation (Eppendorf) for 30 minutes at $14,000 \times g$. at 4° C. After removal of the supernatant, the DNA pellet was dried using a Savant Speedvac vacuum centrifuge. Following ethanol precipitation, the DNA was dissolved in 10 µl TE buffer (10 mM Tris-HCl pH 8.0; 1 mM EDTA; pH 8.0) and the concentration was determined by agarose electrophoresis, using lambda DNA with a known concentration as a reference and ethidiumbromide staining to detect the DNA.

Example 2.3

Cloning of *Aspergillus tubigensis* DNA Fragments into Bacteriophage Lambda EMBL 3

Fragments obtained by partial digestion of genomic DNA, as described in Example 2.2 were ligated in bacteriophage lambda EMBL 3 BamHI arms, obtained from Promega, by the following procedure: 4 µl (2 µg) EMBL 3 DNA, 1 µl (50 ng) genomic DNA fragments, 0.75 µl 10×ligation buffer (Maniatis et al., 1982, pp. 474: 660 mM Tris-HCl; 50 mM $MgCl_2$; 50 mM dithiothreitol; 10 mM ATP; pH 7.6), 0.75 µl 10 mM ATP and 2 µl (1.5 U/µl) $T_4$ DNA ligase (BRL) were pipetted, carefully mixed and incubated for 6 hours at 14° C. After this incubation period, 1 µl $T_4$ DNA ligase was added to the reaction mixture, and the reaction was continued for an additional 4 hours at room temperature.

The ligated DNA was packaged in vitro using Gigapack II Gold packaging extract (Stratagene) and plated on *E. coli* LE392 (Murray, 1977) using NZYCM medium (per 1000 ml: 10 g NZ amine; 5 g NaCl; 5 g yeast extract; 1 g casamino acids; 2 g $MgSO_4.7H_2O$; pH 7.5; for plates 12 g agar is added), according to the manufacturer's instructions.

The complete reaction described above was repeated once, using 3 µl genomic DNA fragments in a final volume of 10 µl.

Example 2.4

Titration and Amplification of the *Aspergillus tubigensis* Genomic Library

Dilutions of the primary genomic library were made in SM buffer (per 1000 ml: 5.8 g NaCl; 2.0 g $MgSO_4.7H_2O$; 50 ml Tris-HCl; pH 7.5; 5 ml 20% gelatin) and plated on *E.coli* LE392 as a host as described by Maniatis et al. (1982, pp. 64) using NZYCM medium. After incubation overnight at 37° C., the resulting plaques were counted and the amount of phages was calculated. The first ligation and packaging resulted in about $7 \times 10^4$ pfu (plaque-forming units), the second in about $4 \times 10^5$ pfu, resulting in a total of about $5 \times 10^5$ pfu.

The thus-obtained genomic library was amplified by plating $5 \times 10^3$ pfu per 85 mm diameter plate (total of five plates) on NZYCM medium as described by Maniatis et al. (1982, pp. 293–294). After incubation overnight at 37° C., the phages were eluted from the resulting confluent plates by adding 5 ml SM buffer. The plates were maintained at 4° C. for 2 hours with intermittent shaking. After removal of the supernatant, the bacteria were removed from the solution by centrifugation at 4,000 g for 10 min. at 4° C. To the supernatant, 0.3% chloroform was added and the number of pfu was determined. This phage stock contained approximately $10^{10}$ pfu/ml.

EXAMPLE 3

Screening of the *Aspergillus tubigensis* Genomic Library for the Endo-xylanase A Gene (Xln A) and Isolation of the Gene

Example 3.1

$^{32}$p-labelling of Synthetic Oligonucleotides

The amino acid sequence derived in Example 1.2 (Formula 1) was used to synthesize oligonucleotide mixes corresponding to the N-terminal amino acid sequence. The oligonucleotides were synthesized by the phosphoramidite method, using an Applied Biosystems oligonucleotide synthesizer.

The oligonucleotide mixes AB801 to AB806 (FIG. 3) were mixed in equal amounts, hereinafter referred to as oligonucleotide mix AB800, to give a final concentration of 37 pmol oligonucleotides per $\mu$l. This oligonucleotide mixture was labelled in a reaction mixture of the following composition: 37 pmol oligonucleotide mixture, 66 mM Tris-HCl pH 7.6, 1 mM ATP, i mM spermidine, 10 mM MgCl$_2$, 15 mM dithiothreitol, 200 $\mu$g/ml BSA, 34 pmol gamma-$^{32}$P ATP (NEN, 6000 Ci/mmol) and 30 U T$_4$polynucleotide kinase (BRL) in a final volume of 50 $\mu$l. The reaction mixture was incubated for 60 min. at 37° C., after which the reaction was terminated by the addition of 4 $\mu$l 0.5 M EDTA; pH 8.0.

Oligonucleotide mixture AB1255, derived from the amino acid sequence obtained in Example 1.3 (Formulas 2 and 3) (FIG. 4), was labelled via the same procedure as described above. The oligonucleotide mixtures were used in the screening of the genomic library (Example 3.2) and in Southern blot analysis (Example 3.4 and 3.5) without further purification.

Example 3.2

Screening of the *Aspergillus tubigensis* Genomic Library for xln A Gene

To screen for the xln A gene in an *Aspergillus tubigensis* genomic library, $3 \times 10^3$ pfu per plate were plated in NZYCM top agarose containing 0.7% agarose (NZYCM medium plus 7 g agarose) on four 85 mm diameter NZYCM (1.2% agar) plates as described by Maniatis et al. (1982, pp. 64). *E. coli* LE392 were used as plating bacteria.

After incubation of the plates overnight at 37° C., two replicas of each plate were made on nitrocellulose filters (Schleicher and Schell BA85) as described by Maniatis et al. (1982, pp. 320–321).

After baking the filters for 2 hours at 80° C., the filters were wetted and washed for 60 minutes at room temperature in $3 \times$ SSC (diluted from $20 \times$ SSC stock solution (per 1000 ml): 175.3 g NaCl; 107.1 g sodium citrate.5.5 H$_2$O; pH 7.0). The filters were prehybridized at 65° C. for two hours in a prehybridization buffer containing: $6 \times$ SSC (diluted from the $20 \times$ SSC stock solution (see above)), 0.5% SDS, $10 \times$ Denhardt's solution (per 5000 ml: 10 g Ficoll-400; 10 g polyvinylpyrrolidone; 10 g Bovine Serum Albumin (Pentax Fraction V)) and 100 $\mu$g/ml heat denatured herring sperm DNA (Boerhinger Mannheim). After two hours prehybridization, the prehybridization buffer was replaced by hybridization buffer which was identical to the prehybridization buffer, except that this buffer did not contain herring sperm DNA, but contained $^{32}$P-labelled oligonucleotide mix AB800, prepared as described in Example 3.1. The filters were hybridized for 18 hours at an final temperature of 38° C., achieved by slow, controlled cooling from the initial temperature of 65° C.

After hybridization, the filters were first washed in $2 \times$ SSC, after which the filters were washed in prewarmed hybridization buffer at 38°°C. for the same period of time. Finally, the filters were washed for 30 minutes at 38° C. in 6 $\times$ SSC, 0.05% sodium pyrophosphate. The air dried filters were taped onto a sheet of Whatman 3MM paper, keying marks were made with radioactive ink and the Whatman paper and filters were covered with Saran Wrap TM. Hybridizing plaques were identified by exposure of Kodak XAR X-ray film for 72 hours at $-70°$ C. using an intensifying screen.

Four of the oligonucleotide mixture hybridizing plaques, appearing in duplicate on the replica filters, were identified and were designated lambda$_{xln1}$ to lambda$_{xln4}$. Each positive plaque was removed from the plate using a Pasteur pipette and the phages were eluted from the agar plug in 1 ml of SM buffer containing 20 $\mu$l chloroform, as described by Maniatis et al. (1982, p. 64). The phages obtained were purified by repeating the procedure described above using filter replicas from plates containing 50–100 plaques of the isolated phages.

After purification, the phages were propagated by plating $5 \times 10^3$ phages on NZYCM medium. After incubation overnight at 37° C., confluent plates were obtained, from which the phages were eluted by adding 5 ml SM buffer and storing the plate for 2 hours at 4° C. with intermittent shaking. After removal of the supernatant, the bacteria were removed from the solution by centrifugation at 4,000$\times$g for 10 minutes at 4° C. Chloroform (0.3%) was added to the supernatent and the number of pfu was determined. These phage stocks contained approximately $10^{10}$ pfu/ml.

Example 3.3

Isolation of DNA From Bacteriophage Lambda

Each of the isolated phages lambda$_{xln1}$ to lambda$_{xln4}$ were propagated as described in Example 3.2 using five plates for each of the phages. The phages were precipitated from the thus-obtained supernatant (25 ml) by addition of an equal volume of a solution containing 20% PEG-6000 (w/v) and 2 M NaCl, followed by thorough mixing and incubation on ice for 60 minutes. The precipitated phages were collected by centrifugation at 14,000$\times$g at 4° C. for 20 minutes. The supernatant was removed by aspiration, while the last traces of liquid were removed using a paper towel. The phages were carefully resuspended in 4 ml SM buffer and extracted once with chloroform.

Prior to extracting the DNA from the phage particles, DNA and RNA originating from the lysed bacteria were removed by incubation of the phage suspension with DNase I and RNase A (both 100 μg/ml) for 30 minutes at 37° C. The phage DNA was subsequently released from the phages by the addition of SDS and EDTA to a final concentration of 0.1% and 20 mM respectively, followed by incubation at 65° C. for 10 minutes. Protein was removed from the solution by extracting twice with an equal volume phenol/chloroform/isoamyl alcohol (25:24:1). After separation of the phases by centrifugation in an Eppendorf centrifuge (14,000×g, 10 min.), the aqueous phase was extracted once with an equal volume chloroform/isoamylalcohol (24:1). The phases were separated by centrifugation (Eppendorf centrifuge, 14,000×g, 10 minutes), after which the DNA was precipitated from the aqueous phase by the addition 0.1 volume 5 M sodium perchlorate and 0.1 volume isopropanol and incubation on ice for 30 min. The DNA was recovered by centrifugation for 10 minutes at 4° C. (14,000×g). The supernatant was removed aspiration, after which the DNA was resuspended in 400 μl TE buffer. The DNA was once again precipitated with ethanol. The DNA was collected by centrifugation for 10 minutes at 4° C. (14,000×g). The supernatant was removed by aspiration, the remaining pellet was briefly dried under vacuum, after which the DNA was resuspended in 125 μl TE buffer containing 0.1 μg/ml RNase A. This purification procedure resulted in the isolation of approximately 40–50 μg DNA from each phage.

Example 3.4

Restriction Analysis of xln A Containing Phages

The isolated DNA of phages lambda$_{xln1}$ to lambda$_{xln2}$ was analyzed by Southern analysis using the following restriction enzymes; BamHI; BglII; EcoRI; HinDIII; KpnI; SalI; SstI; XbaI and XhoI. The DNA was digested for 3 hours at 37°°C., in duplicate, in a reaction mixture composed of the following solutions; 3 μl DNA solution; 1 μl 1 0.5 M spermidine; 5 μl of the appropriate 10×React buffer (BRL); 20 U Restriction enzyme (BRL) and sterile distilled water to give a final volume of 50 μl. After digestion, the DNA was precipitated by the addition of 0.1 volume 3 M NaAc and 2 volumes ethanol. The DNA was collected by centrifugation for 10 minutes at room temperature (14,000×g). The supernatant was removed by aspiration. The remaining pellet was briefly dried under vacuum and resuspended in sterile distilled water. After addition of 4 μl DNA loading buffer (0.25% (w/v) bromophenol blue; 0.25% (w/v) xylene cyanol; 15% (w/v) Ficoll type 400 in H$_2$O), the samples were incubated for 10 minutes at 65°°C. and rapidly cooled on ice. The samples were then loaded on a 0.6% agarose gel in 1×TAE buffer. The DNA fragments were separated by electrophoresis at 25 V for 15–18 hours.

After electrophoresis, the DNA was denatured and transferred to a nitrocellulose membrane as described by Maniatis et al. (1982, pp. 383–386), followed by subsequent prehybridization and hybridization using the labelled oligonucleotide mixes AB800 and AB1255 as described in Example 3.1 and hybridization conditions as described in Example 3.2. The hybridization pattern for each oligonucleotide mixture was obtained by exposure of Kodak XAR-5 X-ray film for 18 hours at −70° C. using an intensifying screen.

From the results, it was concluded that the DNA of all four isolated clones hybridized with the oligonucleotide mixture derived from the N-terminal amino acid sequence (mix AB800), as well as with the oligonucleotide mixture derived from the amino acid sequence obtained from the peptide isolated after *S. aureus* V8 digestion (AB1255). In all four clones, fragments originating from the same genomic region were found.

Figure 5:
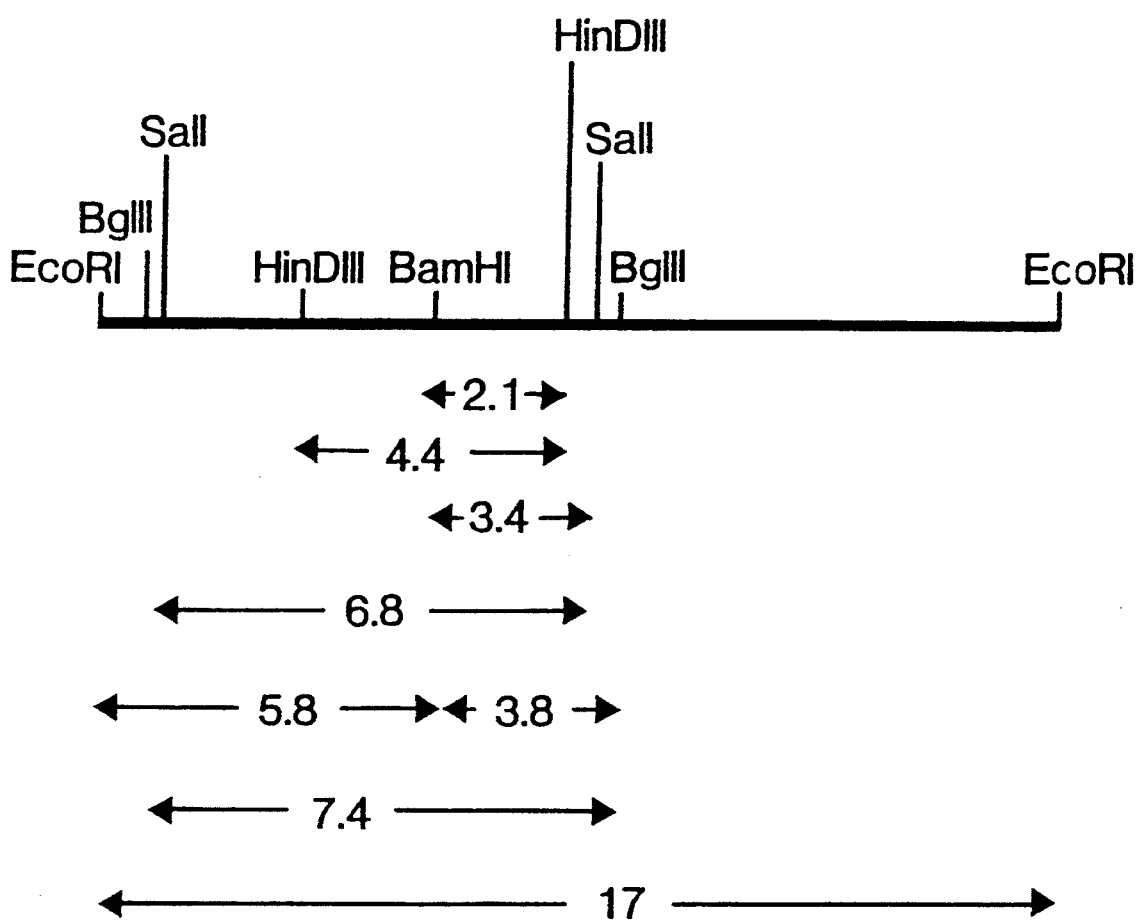
FIG. 5: Restriction map of the genomic region containing the xln A gene, as derived from Southern blot analysis of bacteriophage lambda$_{xln3}$. Indicated are the hybridizing fragments and their corresponding lengths.

The restriction fragment patterns and the hybridization patterns were used to construct an approximate restriction map of the genomic region where the xln A gene is located (FIG. 5).

Example 3.5

Subcloning of the xln A Gene

The 6.9 kb SalI fragment was isolated from phage lambda$_{xln3}$ as described in Example 2.2. This fragment was ligated in the vector pUC9 digested with SalI and dephosphorylated with alkaline phosphatase prepared as follows: 1 μl (1 μg/μl) pUC9 was mixed with 2 μl 10×React 10 (BRL), 1 μl (1 U/μl) SalI and 16 μl sterile distilled water. The DNA was digested for 1 hour at 37° C., after which 0.5 μl alkaline phosphatase (1 U/μl) (Pharmacia) was added, followed by further incubation at 37° C. for an additional 30 minutes. The linearized vector was isolated from a 0.6% agarose gel as described in Example 2.2.

The 6.9 kb SalI fragment was ligated in the SalI digested, dephosphorylated pUC vector via the following procedure: 100 ng pUC fragment was mixed with 100 ng 6.9 kb Sal I fragment and 4 μl 5×ligation buffer (500 mM Tris-HCl, pH 7.6; 100 mM MgCl$_2$; 10 mM ATP; 10 mM dithiothreitol; 25% PEG-6000) and 1 μl (1.2 U/μl) DNA ligase (BRL) was added to this mixture, resulting in a final volume of 20 μl. The resulting plasmid was designated pIM100. After incubation for 16 hours at 14° C., the mixture was diluted to 100 μl with sterile water. 10 μl of the diluted mixture was used to transform *E. coli* JM101 (Yanisch-Perron et al., 1985) competent cells, prepared by the CM1, CM2 method as described in the Pharmacia Manual for the M13 cloning/sequencing system. *E. coli* JM101 containing plasmid pIM100 was deposited at the Centraal Bureau voor Schimmelcultures, Baarn, The Netherlands on Jul. 19, 1990 and was assigned the designation CBS 322.90.

A selection of six of the resulting colonies was grown overnight in LB medium (per 1000 ml: 10 g trypticase peptone (BBL); 5 g yeast extract (BBL); 10 g NaCl; 0.5 mM Tris-HCl; pH 7.5) containing 100 μg/ml ampicillin.

Plasmid DNA was isolated from the cultures by the alkaline lysis method as described by Maniatis et al. (1982, pp. 368–369). This plasmid DNA was used in restriction analysis, as described in Example 3.4 to select a clone harboring the desired plasmid. Plasmid DNA was isolated on a large scale from 500 ml cultures *E. coli* JM101 containing the plasmid pIM100 grown in LB medium containing 100 μg/ml ampicillin (Maniatis et al., 1982, p.86) The plasmid was purified by CsCl centrifugation, phenolized, ethanol precipitated and dissolved in 400 μl TE. The yield was approximately 500 μg.

Figure 7:
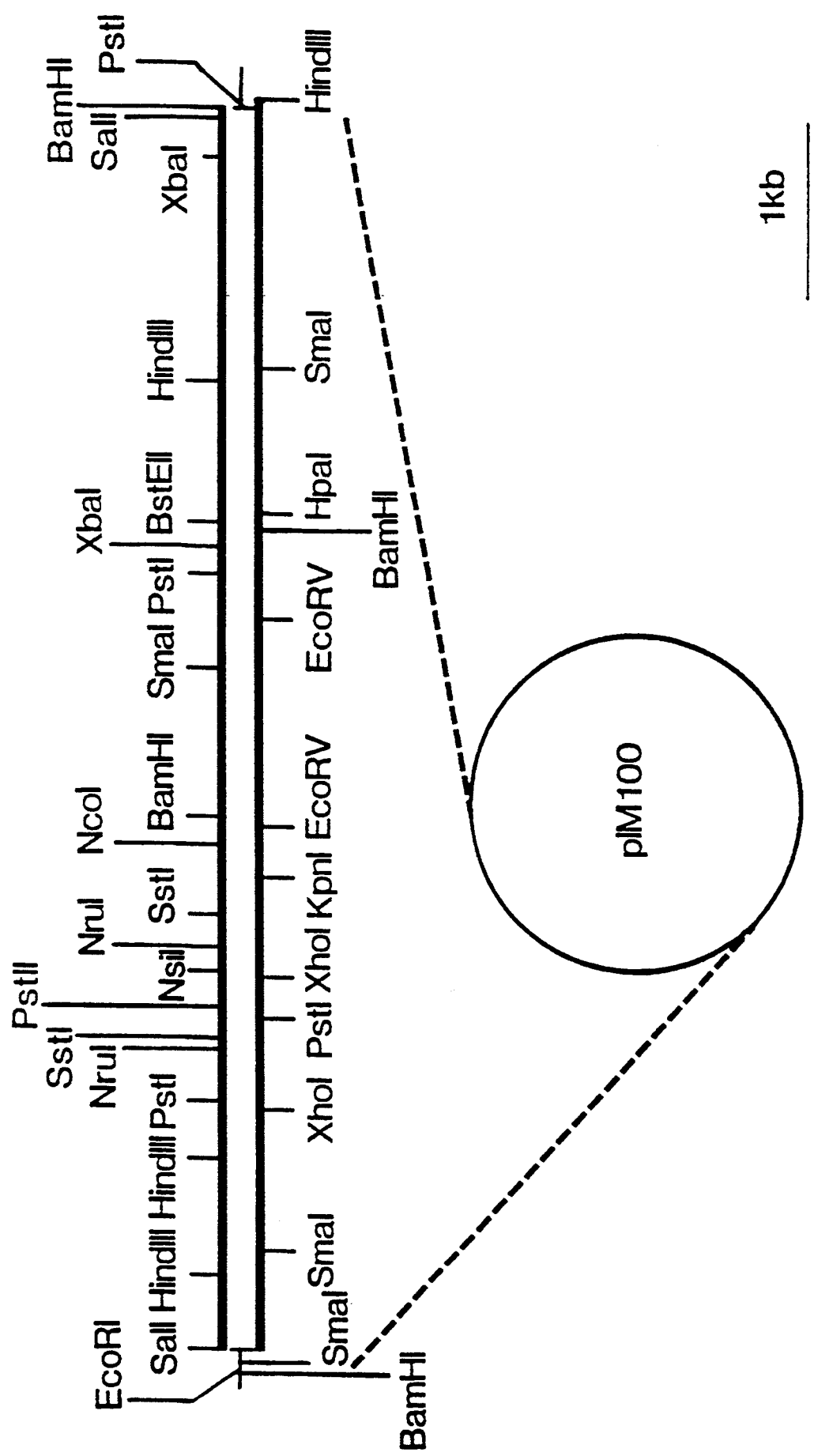
FIG. 7: Restriction map of pIM100 containing the 6.9 kb SalI fragment containing the *Aspergilus tubigensis* xln A gene. In addition to the two HinDIII sites indicated, two further HinDIII sites are present in the plasmid insert.

The plasmid pIM100 was further analyzed by restriction enzymes resulting in the restriction map shown in FIG. 7. The orientation of the gene, as indicated, was determined from hybridization experiments under conditions described in Example 3.2 using the oligonucleotide mixes AB800 and AB1255 as probes.

EXAMPLE 4

Characterization of the *Aspergillus tubigensis* xln A Gene

Example 4.1

Sequence Determination of the *A. tubigensis* xln A Gene

The sequence of the *Aspergillus tubigensis* xln A gene, which comprises its promoter/regulation region, the structural gene and the termination region, was determined by subcloning fragments from pIM100 in M13mp18/mp19, in combination with the use of specific oligonucleotides as primers in the sequencing reactions.

Figure 6:
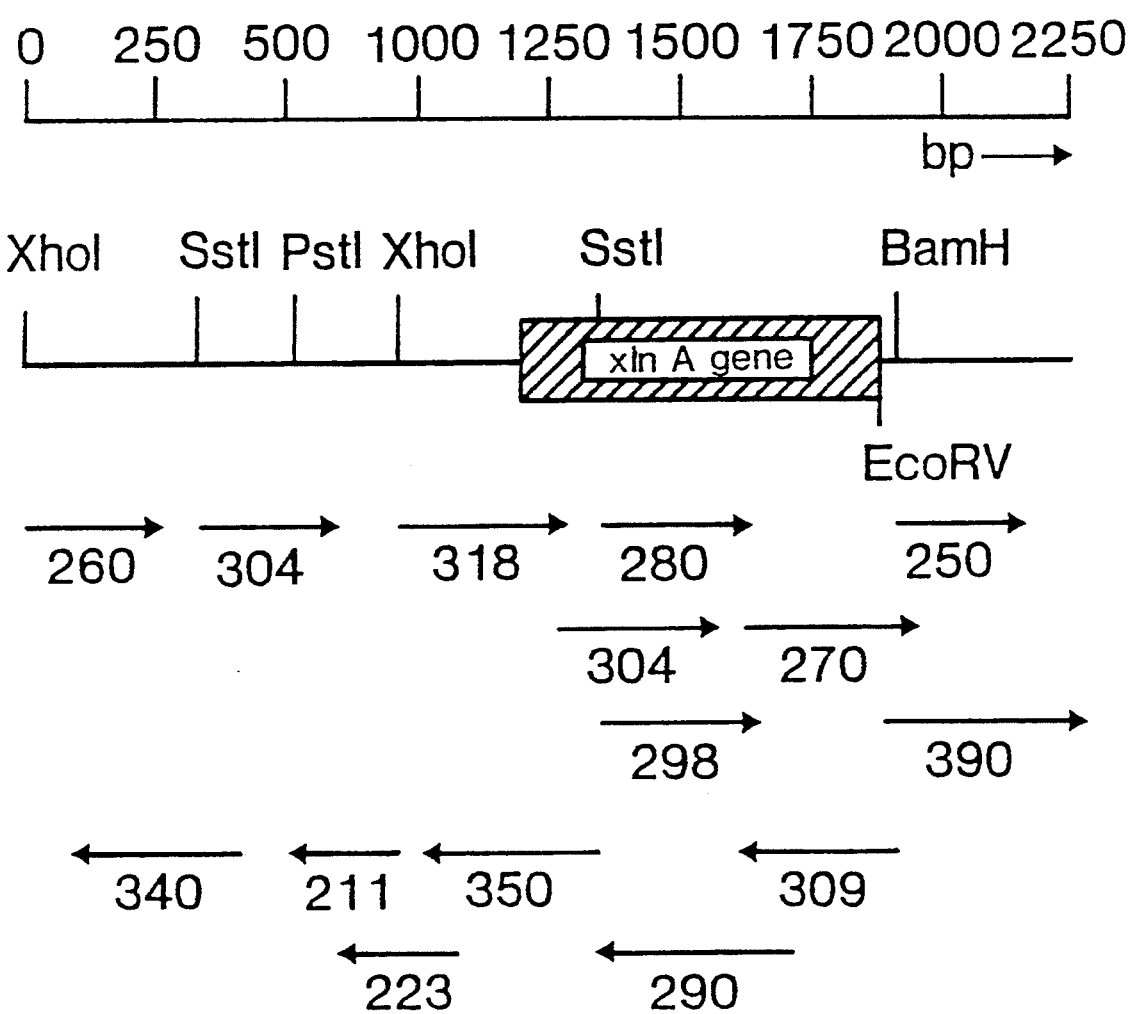
FIG. 6: Strategy employed to sequence the *Aspergillus tubigensis* xln A gene. The arrows indicate the direction and number of bp sequenced.

For nucleotide sequence analysis, restriction fragments were isolated as described in Example 2.2 and were then cloned in bacteriophage M13 mp18/mp19 RF DNA vectors (Messing, 1983; Norrander et al., 1983), digested with the appropriate restriction enzymes. The nucleotide sequences were determined by the dideoxynucleotide chain-termination procedure (Sanger et al., 1977) using the Pharmacia $T_7$ DNA polymerase sequencing kit. The strategy employed to sequence the xln A gene is shown in FIG. 6. Computer analysis of the resulting data was performed using the PC/GENE program (Intelligenetics, Inc.; Madison Wis.). The sequence determined is given in FIG. 8.

Example 4.2

The *A. tubigensis* xln A Gene

The sequence obtained comprises 2054 bp, 949 bp in the 5' non-coding region and 420 bp in the 3' non-coding region. In the 5' upstream region, a putative TATA box (TATAAAT) was found at position 848 to position 854, before the translation initiation site (position 950). A triplicate repeating sequence (SEQ III NO: 14) (5'GTCCATTTAGCCA3') was found in the region 190 to 350 bp from the translation initiation site (positions; 618 to 632; 636 to 650; 656 to 670).

The structural section of the xln A gene is 681 bp long and is interrupted by a single putative intron 48 bp long. The polypeptide derived from the sequence is 211 AA in length. A 17 AA long hydrophobic signal sequence is found at the N-terminus of this polypeptide, which is followed by a pro-peptide which is 12 residues long. The mature protein is 184 AA in size with an predicted molecular weight of 19 kDa and has a theoretical IEP of 3.6.

EXAMPLE 5

Expression of the xln A Gene in an *Aspergillus niger* N593

Example 5.1

Introduction of the xln A Gene into Aspergillus niger N593 by Co-transformation

The plasmid pIM100, obtained in Example 3.5 was introduced in *Aspergillus niger* by co-transformation of *Aspergillus niger* N593 (pyr− mutant of *A. niger* N402; Goosen et al., 1987) using the *Aspergillus niger* pyr A gene as a selective marker on the plasmid pGW635 (Goosen et al., 1989) and the plasmid pIM100 as the co-transforming plasmid.

Protoplasts were prepared from mycelium by growing *Aspergillus niger* N593 on minimal medium supplemented with 0.5% yeast extract, 0.2% casamino acids, 50 mM glucose and 10 mM uridine for 20 hours at 30° C. The preparation of protoplasts of *Aspergillus niger* N593 and the transformation procedure was performed as described by Goosen et al. (1987). The resulting PYR+ transformants were then analyzed for the expression of the xln A gene.

Example 5.2

Screening of Transformants for the Expression of the xln A Gene

The transformants obtained in Example 5.1 were analyzed for the formation of the xln A gene product, the XYL A protein. Twenty transformants were selected and grown for 72 hours on medium containing (per liter): 30 g oat spelt xylan (Sigma); 7.5 g $NH_4NO_3$, 0.5 g KCl, 0.5 g $MgSO_4$, 15 g $KH_2PO_4$, and 0.5 g yeast extract (pH 6.0 ) . After growth, the mycelium was removed by filtration and the culture filtrate was analyzed by SDS-polyacrylamide gel electrophoresis, using a gel containing 12% acrylamide. The XYL A protein was detected on nitrocellulose after electroblotting and incubation with polyclonal antibodies raised against the XYL A protein, which was purified as described in Example 1.1. The antibody bound, was detected after incubation with goat-anti-rabbit antibody conjugated to alkaline phosphatase, according to the Biorad instruction manual.

Sixteen of the twenty transformants analyzed produced the XYL A protein as detected by this procedure. The protein was secreted into the medium. Of the transformants analyzed, transformant TrX9 was selected by I.E.F. analysis, using a pH gradient of pH 3 to 7 and subsequent staining of a dilution series of transformants TrX2 and TrX9, using the method as described by Biely et al. (1985 a and b).

Figure 9:
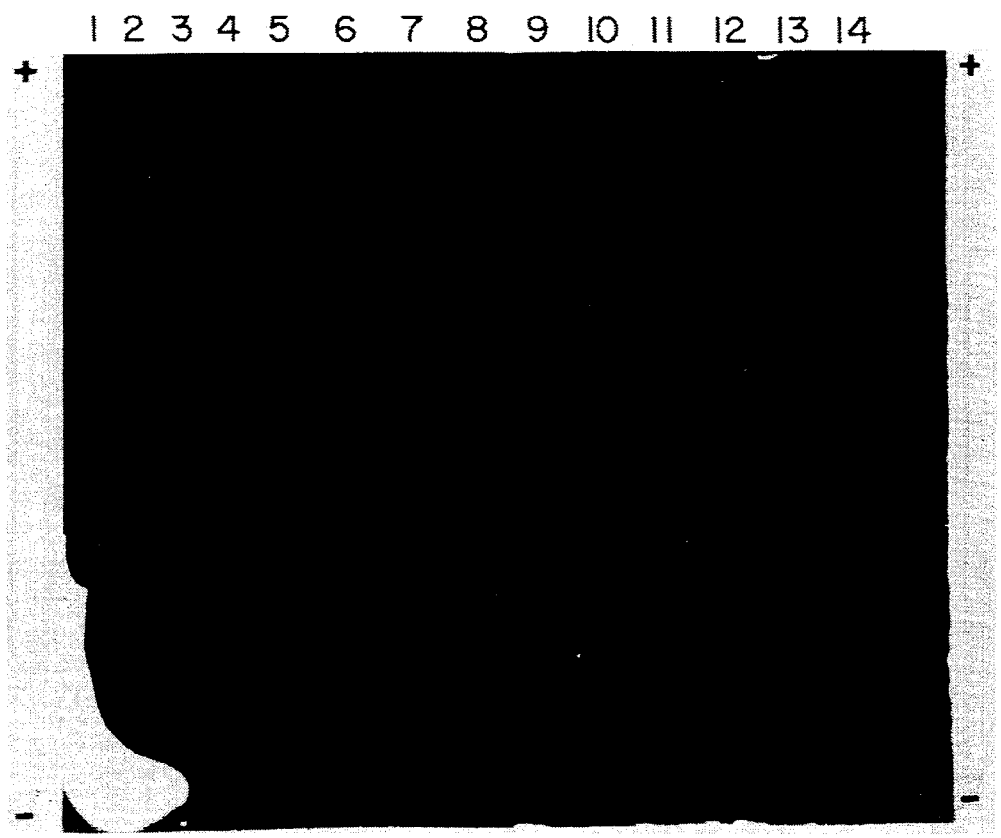
FIG. 9: Representation of a zymogram exhibiting the XYL A protein expressed by transformants TrX2 and TrX9.

FIG. 9 is a zymogram exhibiting the XYL A protein expressed by transformants TrX2 and TrX9.

SDS-PAGE analysis was performed using 4 µl supernatant samples of individual transformants and the *A. niger* control strain, first adjusted to pH 7 with 3 N NaOH and subsequently brought to a final volume of 20 µl with 1×SB buffer, as described by Laemmli (1970). After heating for 5 minutes at 100° C., total mixtures were subjected to a SDS/12.5% polyacrylamide gel electrophoresis and subsequently stained with coomassie brilliant blue. As shown in FIG. 10B, a protein band having an apparent molecular weight of 25 kDa (comparable with purified xylanase (lane 2) could be detected in transformants TrX2 (lane 4) and TrX9 (lane 5), which is absent from the supernatant of the control strain (lane 3). Molecular weight markers (lane 1) represent 92, 68, 46 and 30 kDa.

Example 5.3

Deletion Analysis of the xlnA Promoter Region

Regulatory elements in the *A. tubigensis* xln A promoter were studied by promoter deletion analysis. A series of five constructs of the xln A gene were made and cloned in combination with the *A. niger* pyr A gene. The pyr A gene allows selection in transformations experiments as described in Example 5.1. In addition, the pyr A gene permits the selection of transformants having a single copy of the plasmid integrated at the Dvr A locus.

Figure 21:
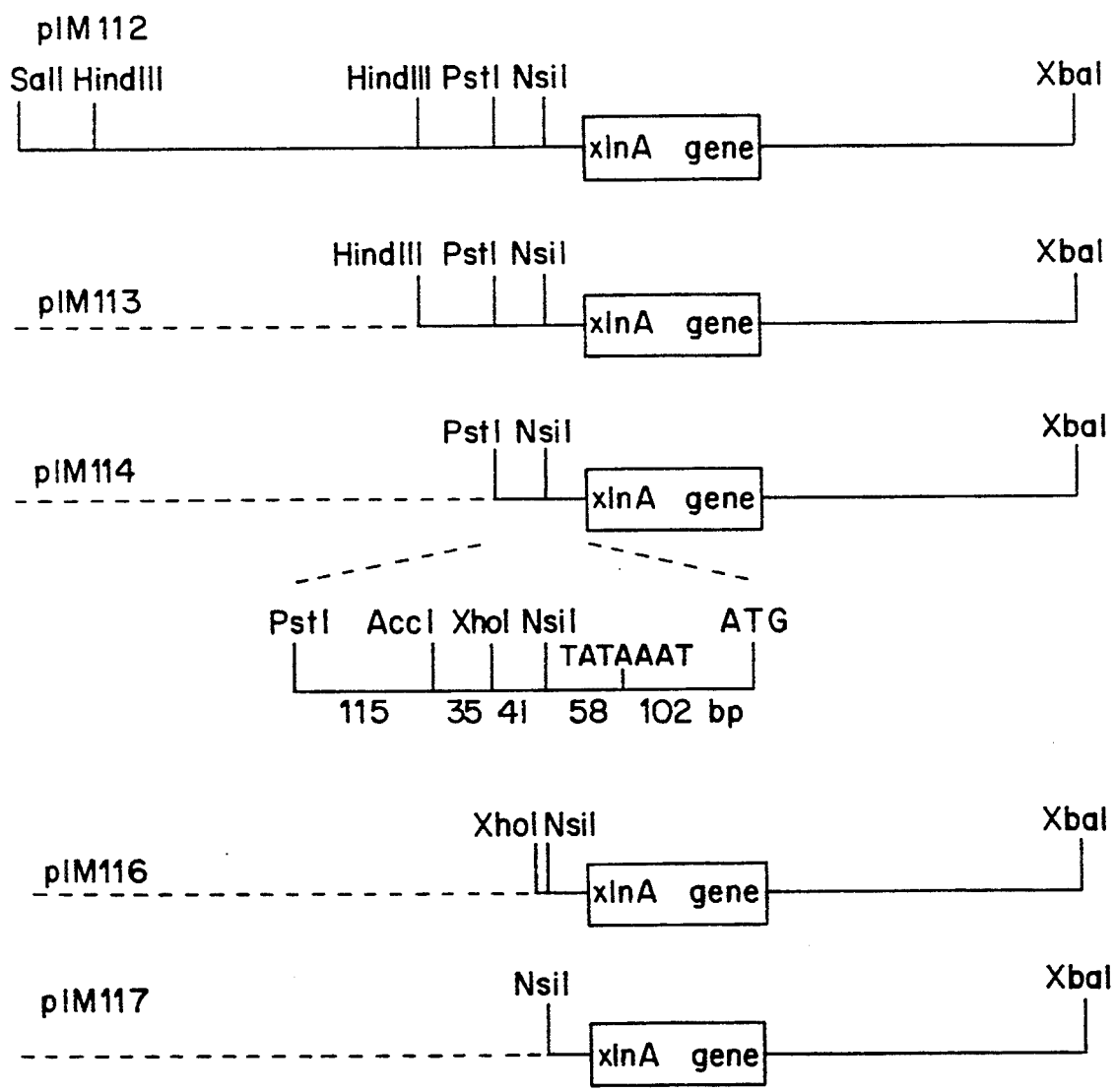
FIG. 21: Schematic representation of the constructs made by creating deletions in the xln A promoter region. For orientation, the XbaI site used in the cloning of the *A. niger* pyr A gene is indicated.

The 4.5 kb SalI/XbaI fragment (FIG. 7) was isolated and ligated into the vector pEMBL18 as described in Example 3.5, resulting in the intermediate plasmid pIM101. In addition to the plasmid pIM101, the following fragments containing the xln A gene were ligated in pEMBL18; the 3.5 kb HindIII/XbaI fragment (resulting in pIM102), the 2.0 kb PstI fragment (resulting in pIM103), the 1.98 kb XhoI/XbaI fragment (resulting in pIM104) and the 1.97 kb NsiI/XbaI fragment (resulting in pIM105). The obtained plasmids were digested using XbaI and ligated to a 3.8 kb XbaI fragment comprising the functional *A. niger* pyr A gene, resulting in the plasmids pIM112, pIM113, pIM114, pIM116 and pIM117 (FIG. 21).

The plasmids pIM112, pIM113, pIM114, pIM116 and pIM117 were used to transform *A. niger* N593 as described in Example 5.1. The resulting PYR+transformants of each plasmid were cultivated and DNA was isolated as described in Example 2.1. The resulting DNA was digested with HDaI and single copy integrations were selected by Southern analysis using a $^{32}$P labelled 3.8 kb XbaI fragment (labelled as described in Example 7.2), which contained the Pyr A gene as a probe. Transformants having a hybridizing HpaI fragment (the size of which was increased by a unit plasmid length as compared to the size of the HpaI fragment in *A. niger* N593) were selected as single copy integrations at the pyr A locus.

Single copy transformants of each of the plasmids, selected as described above, were grown for 36 hours as described in Example 5.2. The expression of the xln A gene was analyzed by IEF analysis as described in Example 5.2 and by Northern analysis after isolation of total RNA as described by de Graaff et al. (1988), using the $^{32}$P labelled 900 bp XhoI/BamHI fragment of the xln A gene as a probe.

In transformants originating from the plasmids pIM112, pIM113 and pIM114, expression of the xln A gene was found as detected by IEF and Northern analysis. However, the transformants originating from the plasmids pIM116 and pIM117 did not express the xln A gens, since neither XYL A protein nor hybridizing RNA were found. From these results it was concluded that the 158 bp PstI/XhoI fragment, the essential difference between pIM114 and pIM116, contains an element necessary for the induction of the xln A gene in *A. niger*, which were grown on medium using xylan as a carbon source.

EXAMPLE 6

Expression in *A. niger* of the xln A Gene Fused to the Promoter and/or Signal Sequence of the *A. niger* Amyloglucosidase (AG) Gene

Example 6.1

Xylanase Expression Vectors

To obtain expression of xylanase in the strain *A. niger* CBS 513.88, additional expression cassettes (pXYL3 and pXYL3AG) were created in which the xln A gene is under the control of the *A. niger* amyloglucosidase (AG) promoter in combination with different signal sequences.

In expression cassette pXYL3, the AG-promoter sequence was fused to the xln A encoding sequence including the xylanase leader.

In the expression cassette pXYL3AG, the AG-promoter sequence, as well as the 18 amino acid (aa) leader sequence of the AG-gene were fused to the xln A gene fragment encoding solely the mature protein.

Example 6.2

Construction of Intermediate Plasmids a) Subcloning the xlnA Locus

Figure 12:
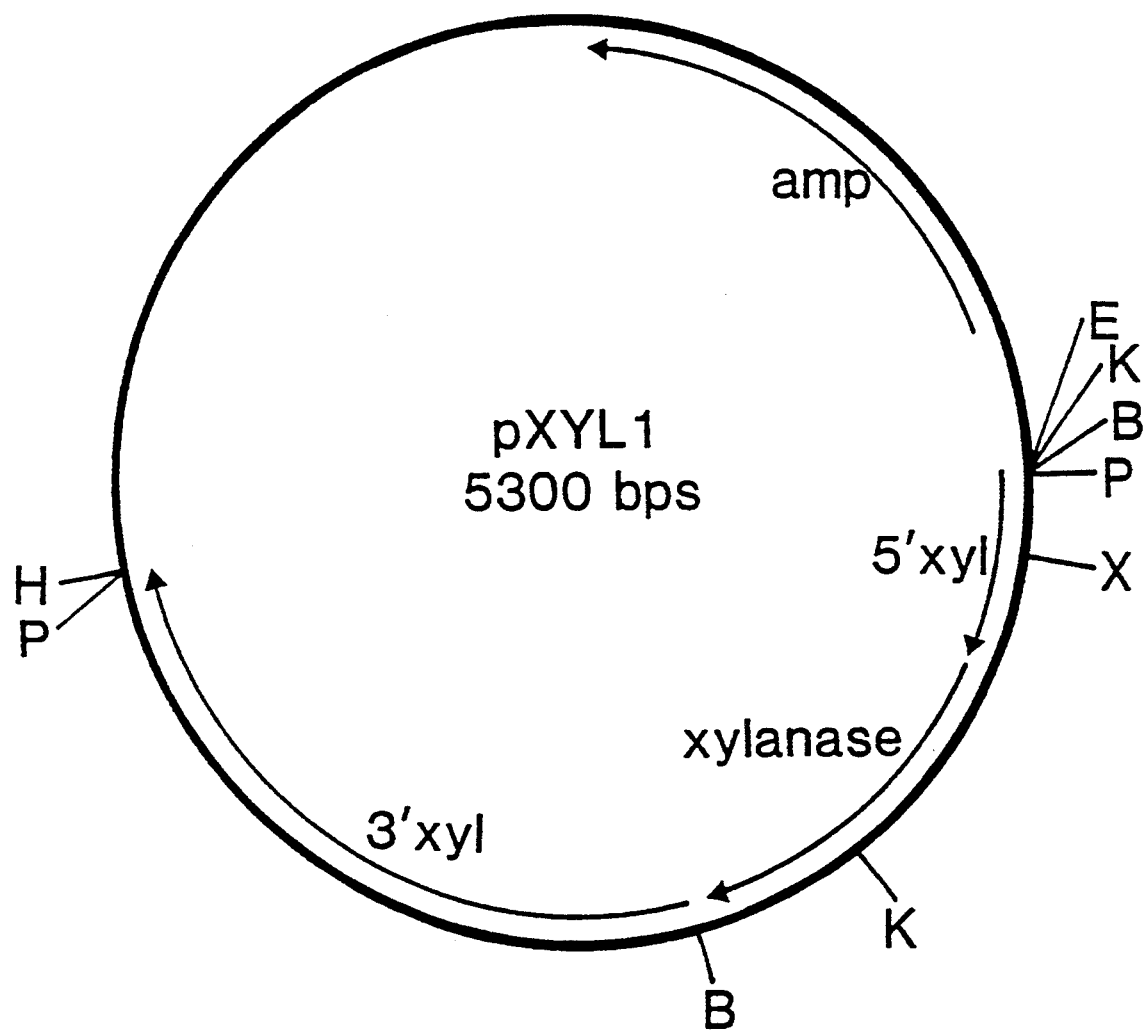
FIG. 12: Physical map of pXYL1 containing the xln A gene on a 2.1 kbp pstI fragment in pTZ18R. [Abbreviations: H=HindIII; P=PStI; B=BamHI; K=KpnI; E=EcoRI; X=XhoI; and S=SalI]

To reduce the length of the genomic xln A locus, the 2 kb pstI fragment of pIM100 (described in Example 3.5) comprising the entire xln A gene including the 5'- and 3' flanking sequences, was subcloned into the PstI site of pTZ18R (Promega). The plasmid containing the xln A gene in the proper orientation (indicated in FIG. 12) was designated pXYL1.

b) Basic Selection Vector pAmdSH

To serve as a selection marker for the transformation of Aspergillus, the EcoRI/Kpn$^I$ DNA fragment of plasmid pGW325 (Wernars, K. (1986)) containing the homologous *Aspergillus nidulans* amdS gene, was inserted into the EcoRI/KpnI sites of pTZ18R (Promega). In the resulting vector (pAmdS), an additional HindIII restriction site was introduced by insertion of the synthetic fragment:

5' AATTCAAGCTTG 3'(SEQ ID NO: 15)

3' GTTCGAACTTAA 5'(SEQ ID NO: 16)

into the EcoRI-site. The thus-obtained plasmid was designated pAmdSH. In this basic vector, the AG/xylanase fusion DNA fragments will be inserted.

c) Isolation of the Genomic AG Locus: Construction of pAB6-1

Plasmid pAB6-1 contains the entire AG locus from *A. niger*, isolated from an *A. niger* plasmid library containing the 13-15 kb HindIII fragments, inserted into pUC19.

For this isolation, the following AG-specific oligonucleotides were used:

AG-1:
5'-GACAATGGCTACACCAGCACC-GCAACGGACATTGTTTGGCCC-3' (SEQ ID NO: 17)

Figure 13:
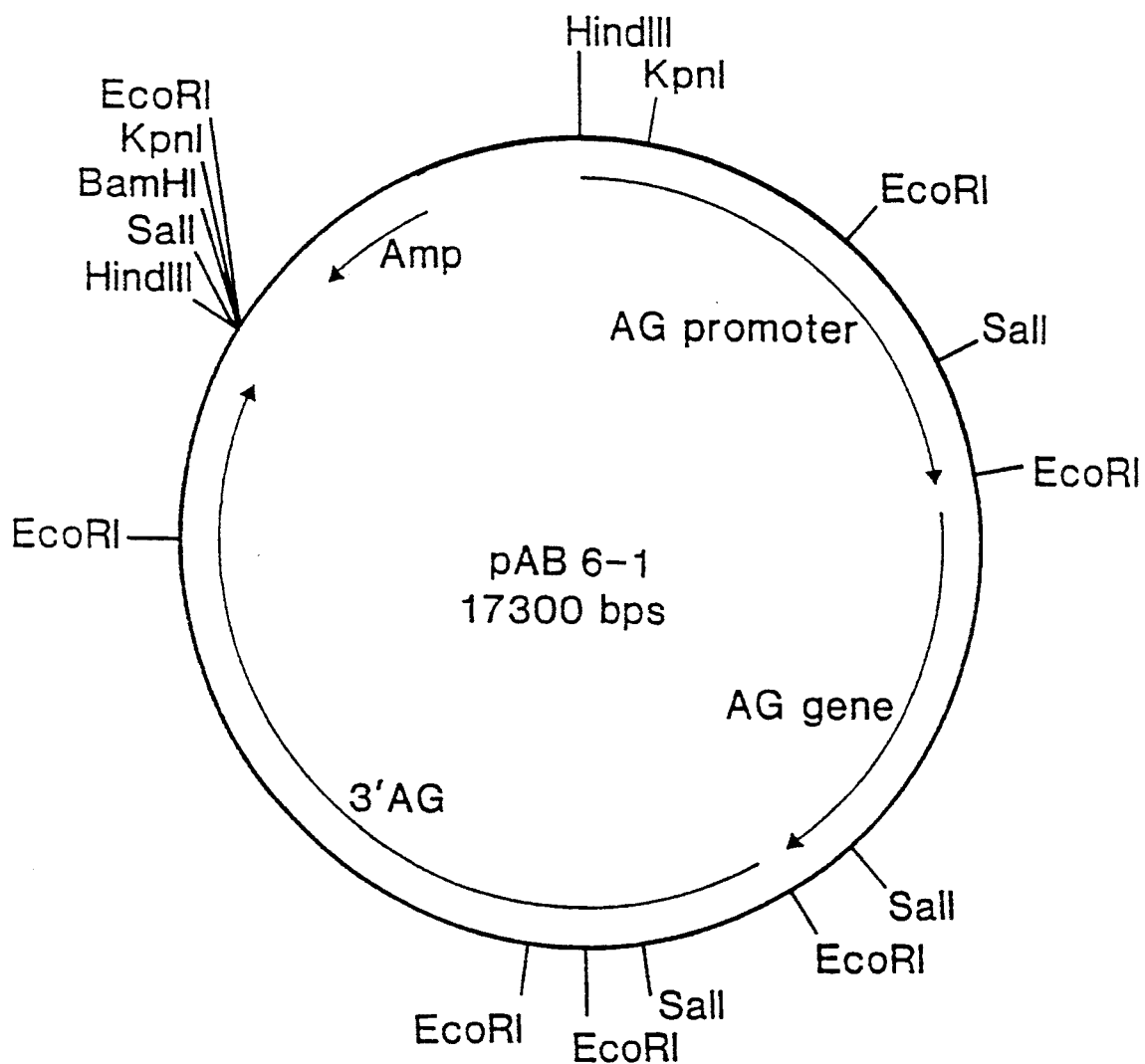
FIG. 13: Physical map of DAB 6-1. The 14.5 kbp HindIII DNA insert in pUC19 contains the entire amyloglucosidase (AG) locus from *A. niger*.

AG-2:
5'-AAGCAGCCATTGCCCGAAGCCGAT-3' (SEQ ID NO: 18)

both based on the nucleotide sequence published for *A. niger* (Boel, et al. (1984a); Boel, et al. (1984b)). The oligonucleotide probes were derived from the sequence surrounding intron 2: oligo AG-1 is located downstream this intron and has a polarity identical to the AGmRNA; oligo AG-2 is found upstream of intron 2 and is chosen antiparallel to the AGmRNA. Plasmid pAB6-1 contains the entire AG locus on a 14.5 kb HindIII fragment (see FIG. 13).

d) The Intermediate Plasmids pXYLAG and pXYL-2AG

Fusion of the AG-promoter and the 18 aa AG-leader sequence to the xln A gene encoding the mature protein (lacking the serine from position 1) was performed by the Polymerase Chain Reaction (PCR) method.

In the PCR reactions, two templates were used: pXYL1, containing the xln A gene and pAB6-1, containing the entire AG genomic locus.

As primers for the PCR DNA-amplifications, four synthetic oligo nucleotides were designed having the following sequence:

Oligo AB 1771:5'—CTCTGCAG<u>GAATTC</u>AAGCTAG—3' (SEQ ID NO: 19)
(an AG specific sequence around the <u>EcoRI</u> site approx.
250 bp upstream from the ATG initiation codon).

Oligo AB 1985:5'—GTAGTTGATACCGGCACTTGCCAACCCTGTGCAGAC—3' (SEQ ID NO: 20)

mature xylanase ――⊥―― 18 aa AG-leader

Oligo AB 1986:5'—GTCTGCACAGGGTTGGCAAGTGCCGGTATCAACTAC—3' (SEQ ID NO: 21)

18 aa AG-leader ――⊥―― mature xylanase

Oligo AB 1984:5'—CCG<u>GGATCC</u>GATCATCACACC—3' (SEQ ID NO: 22)
(a <u>xln</u> A specific sequence located at the <u>BamHI</u> site
on position 1701 as shown in Figure 8).

The PCR was performed as described by Saiki et al. (1988) and according to the supplier of TAQ-polymerase (Cetus). Twenty-five amplification cycles (each: 2 minutes at 55° C.; 3 minutes at 72° C.; 1 minute at 94° C.) were carried out in a DNA-amplifier (Perkin-Elmer/Cetus).

Figure 14:
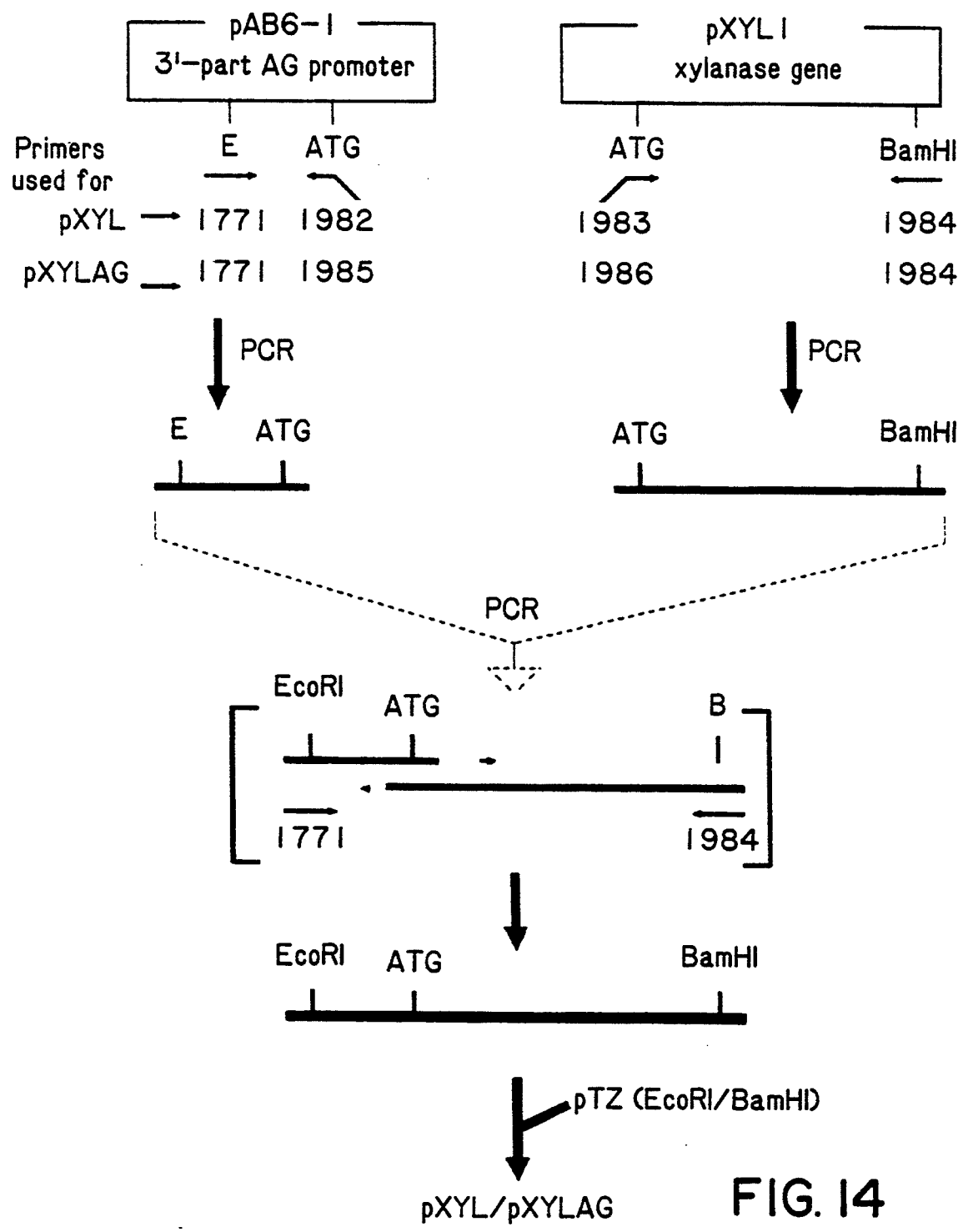
FIG. 14: A schematic view of the generation of AG promoter/xylanase gene fusions performed by the polymerase chain reaction.

To fuse the AG sequences to the xln A coding sequence, two separate polymerase chain reactions were performed: the first reaction with pAB6-1 as the template and oligonucleotides AB 1771 and AB 1985 as primers to amplify a 300 bp DNA fragment which contained the 3' piece of the AG-promoter and the 18 aa AG-leader sequence, flanked at the 3'-border by the first 18 nucleotides of the coding sequence of-xln A and the second reaction with pXYL1 as the template and oligonucleotides AB 1986 and 1984 as primers to amplify xln A DNA sequences encoding the mature xylanase protein, flanked at the 5'-border by the last 18 nucleotides of the AG-signal peptide. A schematic view of these amplifications is presented in FIG. 14.

The two DNA fragments generated were purified by agarose gel electrophoresis and ethanol precipitation and subsequently used as templates in the third PCR with oligo nucleotides AB 1771 and 1984 as primers to generate the AG-xylanase fusion. The thus-obtained DNA fragment was digested with EcoRI and BamHI and subcloned into the appropriate sites of pTZ18R. The resultant fusion was sequenced and designated pXYLAG (see FIGS. 14 and 15).

Figure 15:
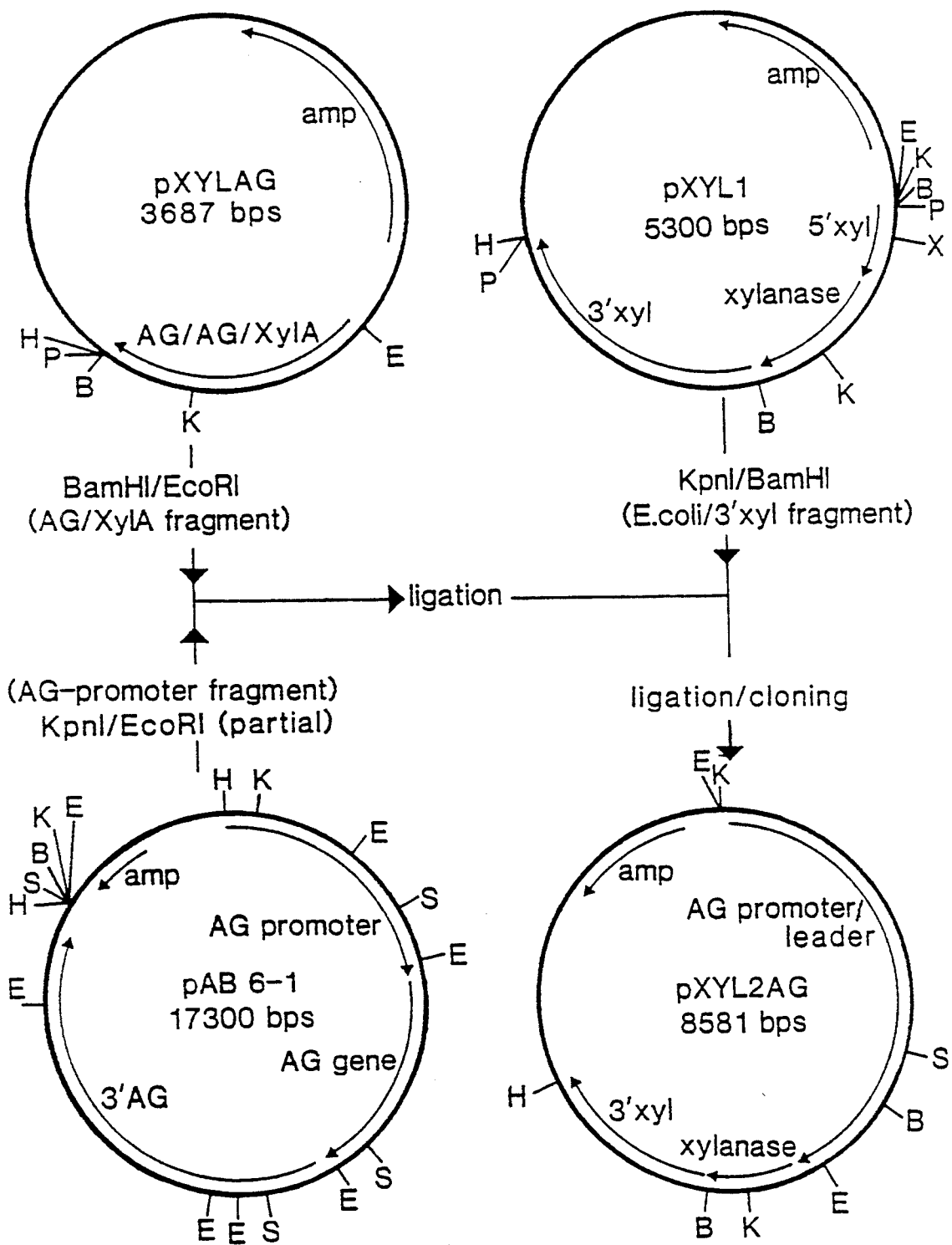
FIG. 15: Construction pathway of the intermediate plasmid pXYL2AG. [Abbreviations: see FIG. 12]

The remaining (3.5 kb) upstream region of the AG-promoter was obtained by digestion of pAB6-1 with KpnI and partially with EcoRI and purified by agarose gel electrophoresis and ethanol precipitated. This 3.5 kb AG DNA promoter fragment was first ligated to the EcoRI/BamHI AG/xylanase fusion fragment of pXYLAG and subsequently molecular cloned in E. coli after ligation into the vector pXYL1, which was digested with KpnI/BamHI and wherefrom the KpnI/BamHI fragment, containing the 5' and coding xln A sequences, was removed. The thus-obtained plasmid pXYL2AG is shown in FIG. 15.

e) The Intermediate plasmids pXyL and pXYL2

Fusion of the AG-promoter sequence to the xln A gene including the xylanase leader was performed as described in part d), above. As primers, two additional oligonucleotides were designed having the following sequence:

Oligo AB 1982: 5'-AGCCGCAGTGACCTTCATTGCTGAGGTGTAATGATG-3' (SEQ ID NO: 23)

Xylanase gene ――⊥―― AG-promotor

Oligo AB 1983: 5'-CATCATTACACCTCAGCAATGAAGGTCACTGCGGCT-3' (SEQ ID NO: 24)

AG promotor ――⊥―― Xylanase gene

To fuse the AG promoter sequence to the xylanase gene (including the xylanase signal sequence)., two separate polymerase chain reactions were performed: the first reaction with pAB6-1 as template and oligonucleotides AB 1771 and AB 1982 as primers to amplify a 282 bp fragment containing the 3'-part of the AG promoter flanked at the 3'-border by 18 nucleotides of the xylanase leader and the second reaction with pXYL1 as template and the oligonucleotides AB 1983 and AB 1984 as primers to amplify a DNA fragment containing the entire xylanase gene (including the xylanase leader) and flanked at the 5'-border by 18 nucleotides of the AG-promoter.

Figure 16:
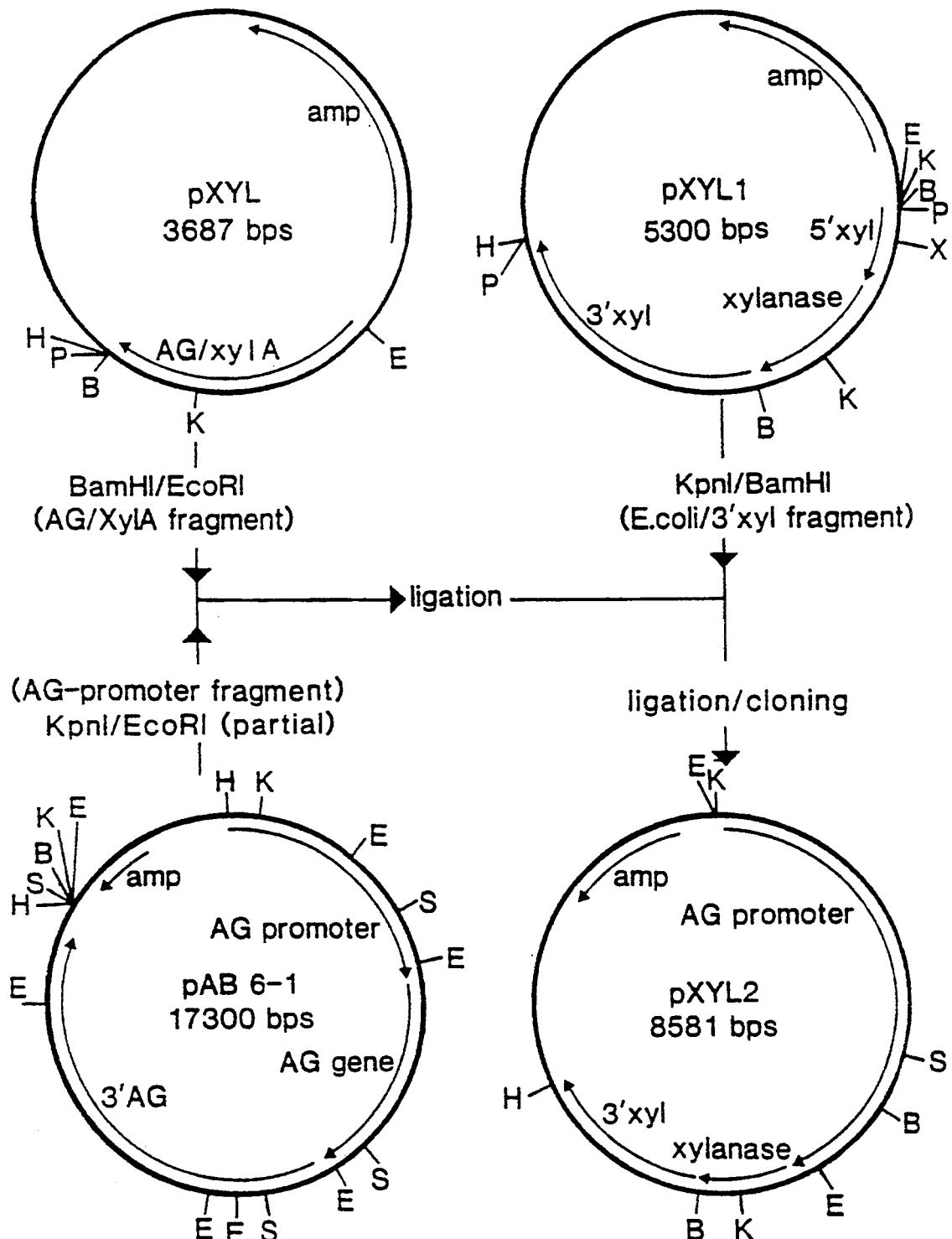
FIG. 16: Construction pathway of the intermediate plasmid pXYL2. [Abbreviations: see FIG. 12]

The two DNA fragments generated were purified by agarose gel electrophoresis and ethanol precipitation and subsequently used as templates in a third PCR with oligonucleotides AB 1771 and 1984 as primers to generate the AG-xylanase fusion. The thus-obtained DNA fragment was digested with EcoRI and BamHI and subcloned into the appropriate sites of pTZ18R. The resultant fusion was sequenced and designated pXYL (see FIGS. 14 and 16).

The remaining (3.5 kb) upstream region of the AG promoter was inserted into pXYL1 as described in part d), above. The thus-obtained plasmid was designated pXYL2.

Example 6.3

Construction of the Xylanase Expression Cassettes pXYL3AG and pXYL3

Figure 17:
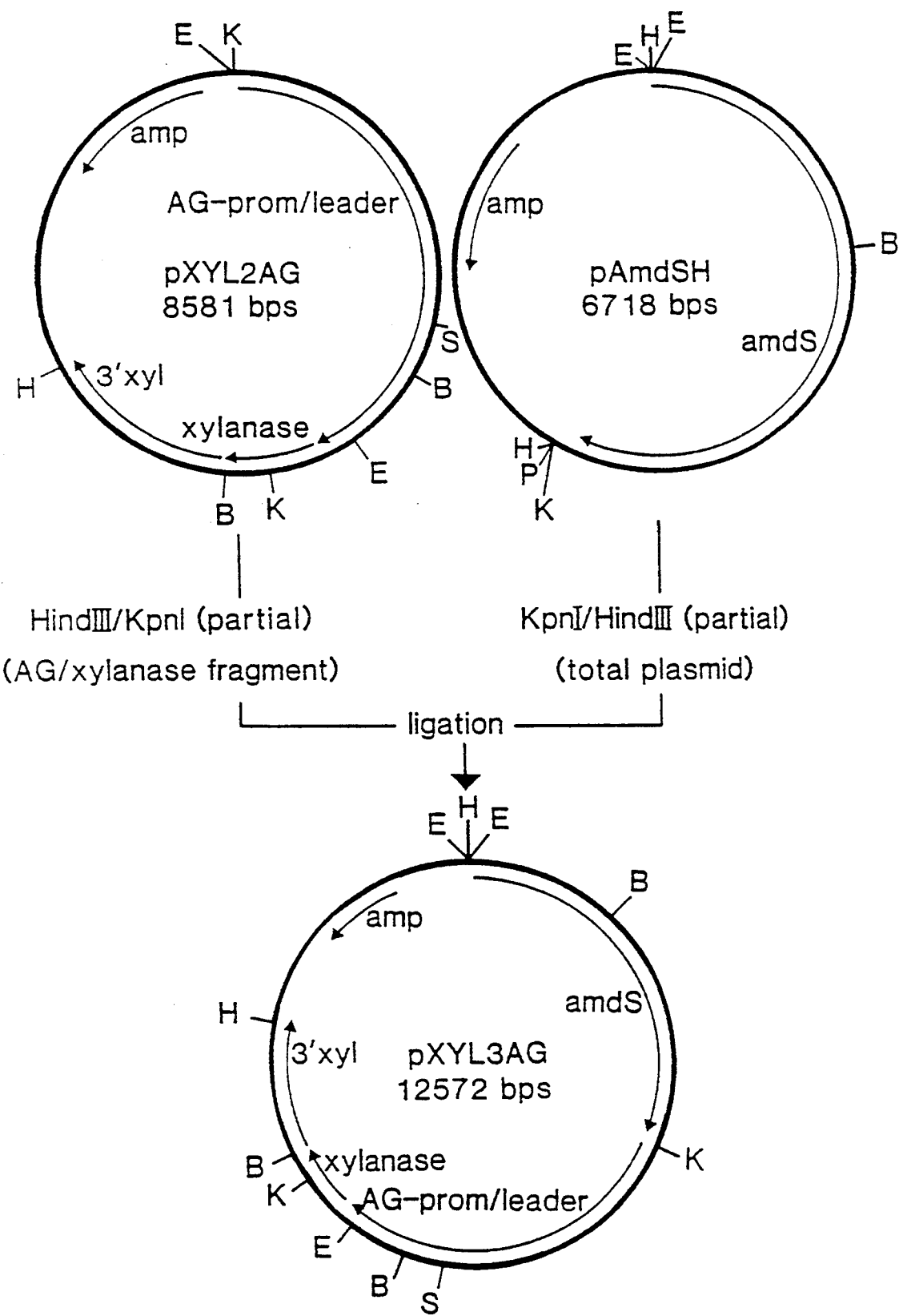
FIG. 17: Construction pathway of the intermediate plasmid pXYL3AG. [Abbreviations: see FIG. 12]
Figure 18:
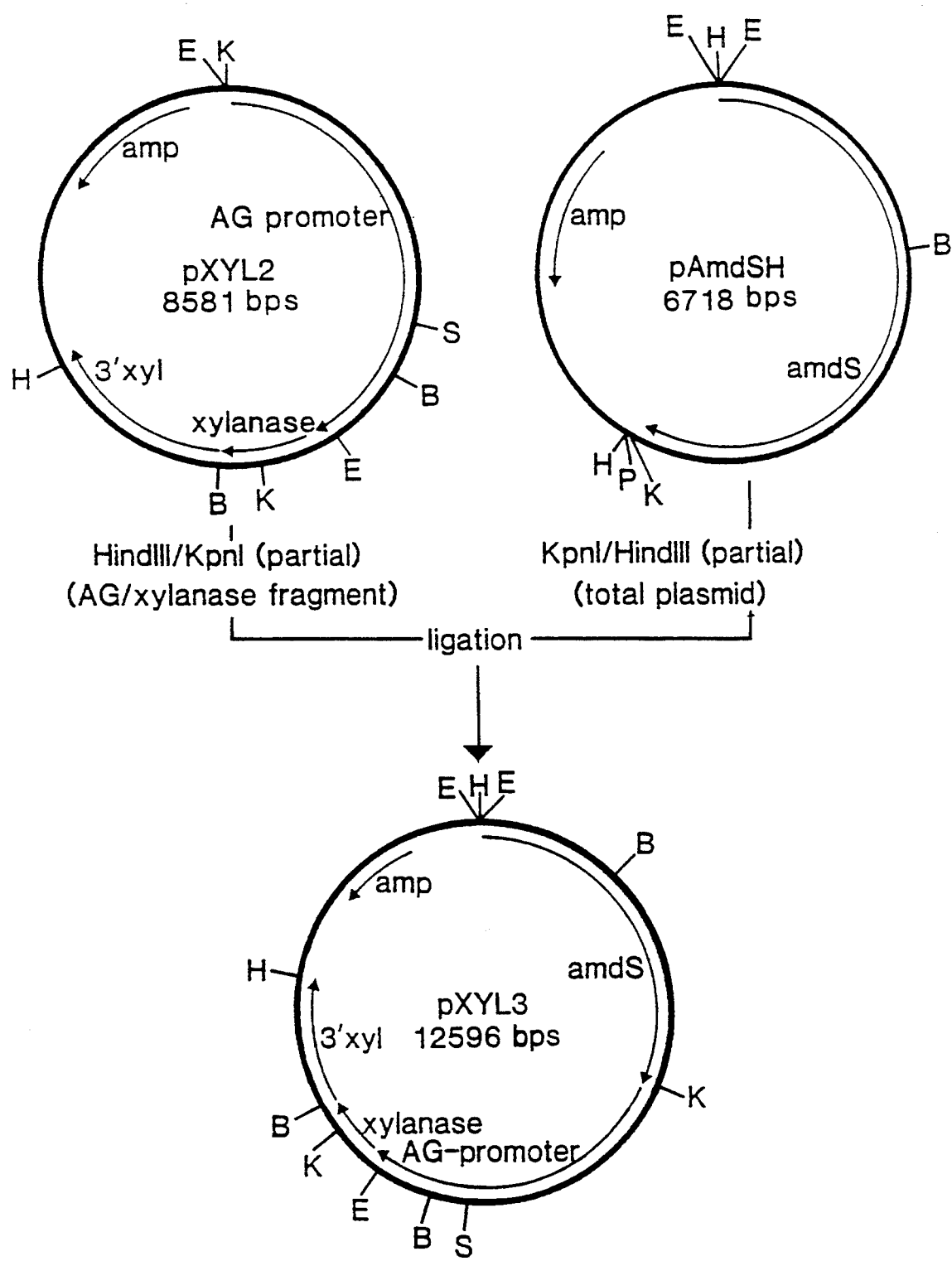
FIG. 18: Construction pathway of the intermediate plasmid pXYL3. [Abbreviations: see FIG. 12]

Both expression cassettes were created by insertion of the AG/xylanase fusions of pXYL2AG or pXYL2 into the basic A. niger vector pAmdSH. For this final construction, pAmdSH was digested with KpnI and HindIII (partially) and pXYL2AG and pXYL2 with HindIII and partially with KDnI. All fragments were isolated and purified by gel electrophoresis and ethanol precipitation. To the 6.8 kb KpnI/HindIII DNA fragment of pAmdSH, either the 5.3 kb KpnI/HindIII DNA fragment of pXYL2AG or pXYL2 was added, ligated and subsequently molecular cloned by transferring both ligation mixtures to *E. coli*. The thus-derived expression cassettes were designated pXYL3AG (containing the AG-leader) and pXYL3 (containing the xylanase leader), as shown in FIGS. 17 and 18, respectively.

Example 6.4

Expression of the xln A Gene Under the Control of the AG Promoter in *A. niger* a) Transformation of *A. niger* (CBS 513.88)

Before transferring both expression cassettes pXYL-3AG and pXYL3 to *A. niger*, the *E. coli* sequences were removed by HindIII digestion, gel electrophoresis and ethanol precipitation. Transformation of the strain *A. niger* (CBS 513.88, deposited October 10, 1988) was performed with 10 μg linearized DNA fragment by procedures as described by Tilburn, J. et al. (1983) and Kelly and Hynes (1985) with the following modifications:

Mycelium was grown on Aspergillus minimal medium (Cove, D. (1966)) supplemented with 10 mM arginine and 10 mM proline for 16 hours at 30° C. in a rotary shaker at 300 rpm.

Only Novozym 234, and no helicase, was used for formation of protoplasts.

After 90 minutes of protoplast formation, 1 volume of STC buffer (1.2 M sorbitol, 10 mM Tris-HCl pH 7.5, 50 mM $CaCl_2$) was added to the protoplast suspension and centrifuged at 2500 rpm at 4° C. for 10 minutes in a swinging-bucket rotor. The protoplasts were washed and resuspended in STC-buffer at a concentration of $10^8$ cells/me.

Plasmid DNA was added in a volume of 10 μl in TE buffer (10 mM Tris-HCl pH 7.5, 0.1 mM EDTA) to 100 μl of the protoplast suspension.

After incubation of the DNA-protoplast suspension at 0° C. for 25 minutes, 200 μl PEG solution was added drop-wise (25% PEG 4000 (Merck), 10 mM Tris-HCL pH 7.5, 50 mM $CaCl_2$). Subsequently, 1 ml of PEG solution ( 60% PEG 4000 in 10 mM Tris-HCl pH 7.5, 50 mM $CaC_2$) was added slowly, with repeated mixing of the tubes. After incubation at room temperature, the suspensions were diluted with STC-buffer, mixed by inversion and centrifuged at 2000 rpm at 4° C. for 10 minutes. The protoplasts were resuspended gently in 200 μl STC-buffer and plated on Aspergillus minimal medium with 10 mM acetamide as sole nitrogen source, 15 mM CsCl, 1 M sucrose, solidified with 0.75% bacteriological agar #1 (Oxoid). Growth was performed at 33° C. for 6–10 days.

b) Growth of Transformants in Shake Flasks

Single *A. niger* transformants from each expression cassette were isolated, and the spores were streaked on selective acetamide-agar plates. Spores of each transformant were collected from cells grown for 3 days at 37° C. on 0.4% potato-dextrose (Oxoid, England) agar plates. Xylanase production was tested in shake flasks under the following growth conditions:

About $1.10^8$ spores were inoculated in 100 ml preculture medium containing (per liter): 1 g $KH_2PO_4$; 30 g maltose; 5 g yeast-extract; 10 g casein-hydrolysate; 0.5 g $MgSO_4.7H_2O$ and 3 g Tween 80. The pH was adjusted to 5.5.

After growing overnight at 34° C. in a rotary shaker, 1 ml of the growing culture was inoculated in a 100 ml main-culture containing (per liter): 2 g $KH_2PO_4$; 7 0 g maltodextrin (Maldex $MDO_3$, Amylure); 12.5 g yeast-extract; 25 g casein-hydrolysate; 2 g $K_2SO_4$; 0.5 g $MgSO_4.7H_2O$; 0.03 g $ZnCl_2$; 0.02 g $CaCl_2$; 0.05 g $MnSO_4.4\ H_2O$ and $FeSO_4$. The pH was adjusted to 5.6. The mycelium was grown for at least 140 hours.

c) Analyses of transformants.

Xylanase analyses of individual transformants were performed by measuring the xylanase activity; by SDS-polyacrylamide gel electrophoresis stained with Coomassie Brilliant Blue and by a zymogram stained with xylan-Remazol brilliant blue R.

Xylanase activities were determined as described by Leathers et al. (1984), with some modification. The substrate concentration was increased from 1% to 5% oat xylan, dissolved in 100 mM NaAc at pH 3.5 and heated to 100° C. for 10 minutes. In addition, enzyme reactions were carried out at 39° C. instead of 30° C.

Xylanase production levels were measured in the supernatant of 6 day-shake flask fermentations of several, randomly chosen transformants obtained from each expression cassette. The results are shown in Table 1.

TABLE 1

Xylanase production of several *A. niger* CBS 513.88 strains transformed with plasmids containing the xlnA gene under the control of the *A. niger* AG-promoter in combination with different leaders.

| Expression cassette | Trasnformant # | Xylanase activity (U/ml) |
|---|---|---|
| pXYL3 | 1.1 | 2400 |
| (AG-promoter/ | 1.2 | 1700 |
| xln-leader) | 10 | 3600 |
|  | 29 | 3500 |
| pXYL3AG | 3.1 | 2400 |
| (AG-promoter/ |  |  |
| AG-leader) |  |  |
| *A. niger* CBS 513.88 | — | 0 |
| (control strain) |  |  |

SDS-PAGE analysis was performed as follows: after 6 days of growth as described in part b) above, 4 μl supernatant samples from individual transformants and from the *A. niger* control strain were first adjusted to pH 7 with 3 N NaOH and subsequently brought to a final volume of 20 μl with 1×SB buffer, as described by Laemmli (1970). After heating for 5 minutes at 100°°C., total mixtures were subjected to a SDS/12.5% polyacrylamide gel electrophoresis and subsequently stained with coomassie brilliant blue. As shown in FIG. 10 A, a protein band having an apparent molecular weight of 25 kDa (comparable with purified xylanase (lane 1) could be detected in transformants 10 (lane 4), 29 (lane 5) and 1.1 (lane 6). This protein band was absent from the supernatant of the control strain (lane 3). Molecular weight markers (lane 2) represent 94, 67, 43 30, 20 and 14.5 kDa.

Zymogram analysis was performed as follows. The same samples as used above were also applied two times to a native 8–25% PAA phast system gel (BRL). Following electrophoresis, gel A was stained with Coomassie brilliant blue (see FIG. 11A) and gel B with a Remazol brilliant blue-xylan (Megazyme) overlay at pH 3.5 as described by Biely et al. (1985a) (see FIG. 11B), to visualize the xylanase activity. Samples supplied to this RBB-xylan overlay gel contained 5 times less protein as compared to the samples provided to the gels as shown in FIGS. 10 and 11 A. The identification of the lanes in FIGS. 11 A and B are the same as FIGS. 10 A and B.

These analyses clearly show the expression and secretion of active endo-xylanase in *A. niger* CBS 513.88 transformed with an expression cassette wherein the xln A gene is under the control of the *A. niger* amyloglucosidase promoter. Expression and secretion were also observed with different *A. niger* signal sequences. Furthermore, the protein lacking the serine residue from position 1 nevertheless retained xylan-degrading activity.

EXAMPLE 7

Screening for Genes Related to the xlnA Gene in *Trichoderma reesei* QM9414

Example 7.1

$^{32}$p-labelling of DNA Fragments 25 ng of a 900 bp XhoI/BamHI fragment isolated from the plasmid pIM100 as described in Example 2.2 was labelled by random priming using the oligonucleotide labelling kit (Pharmacia) according to the manufacturer's instructions. To remove the unincorporated α-$^{32}$P-dATP from the mixture, the volume was increased to 100 μl with TE buffer, after which the α-$^{32}$P-dATP was removed by fractionation on a Sephadex G50 column. Fractions containing the radioactively labelled DNA were denatured by incubation for three minutes at 100° C., and kept single stranded by rapid chilling on ice, before addition to a hybridization buffer containing 6×SSC; 5× Denhardt's solution; 0.1% sodium pyrophosphate and 100 μg/ml heat denatured herring sperm DNA.

Example 7.2

Genomic Hybridization of *T. reesei* QM9414 DNA

High molecular weight DNA isolated from *T. reesei* as described in Example 2.1 was digested with BamHI, BglII, EcoRI and SalI. The resulting fragments were separated by agarose gel electrophoresis and transferred to nitrocellulose membrane as described by Maniatis et al. (1982, pp. 383-389). The nitrocellulose membranes were prehybridized at 57° C. for two hours in hybridization buffer (as described in Example 7.1, above). After this prehybridization process, the radioactively labelled fragment, described in Example 7.1, was added to the hybridization buffer and the hybridization was continued for 44 hours. After hybridization, the filters were washed for 90 minutes at 57° C. in 4×SSC; 0.1% SDS; 0.1% sodium pyrophosphate, followed by a final washing using 2×SSC at the same temperature. After taping the membranes to Whatman 3MM paper and properly marking with radiolabelled ink, the filters were covered with Saran Wrap ™ and autoradiographed for 72 hours at −70° C. using Kodak XAR-5 X-ray film and Kodak X-Omatic cassettes with regular intensifying screens.

The hybridization fragments found are summarized in Table 2.

TABLE 2

Hybridizing fragments and their lengths (kbp) found in *T. reesei* genomic DNA using a fragment of the *A. tubigensis* xln A gene as a probe

| BamHI | BglII | EcoRI | SalI |
|---|---|---|---|
| 16 | 18* | 18* | 6.8*[1] |
| 13* | 9.4 | 4.2 | 3.8 |
| 4.0 | (7.3) | | |

TABLE 2-continued

Hybridizing fragments and their lengths (kbp) found in *T. reesei* genomic DNA using a fragment of the *A. tubigensis* xln A gene as a probe

| BamHI | BglII | EcoRI | SalI |
|---|---|---|---|
| | | 4.2 | |

\* = Strongest hybridizing fragment
[1] = Double bands
( ) = Very weak signal

Example 7.3

Screening of the *Trichoderma reesei* Genomic Library for xln A-related Genes

The hybridization conditions chosen to screen the Trichoderma reesei genomic library for xln A-related genes using the $^{32}$P labelled 900 bp XhoI/BamHI fragment, containing the xln A gene as a probe, as described in Examples 6.1 and 6.2, were: prehybridization in 6×SSC, 0.1% SDS, 0.05% sodium pyrophosphate and 100 μg/ml denatured herring sperm DNA at 60° C. for 3–5 hours; followed by hybridization in 6×SSC, 0.1% SDS, 0.05% sodium pyrophosphate and 100 μg/ml denatured herring sperm DNA at ° C. for 44 hours; followed by two washes in 5×SSC, 0.1% SDS at 60° C. and two washes in 3×SSC at 60° C. After transfer of the filters to 3 MM paper and proper marking with radiolabelled ink, the filters were covered with Saran wrap and exposed for 72 hours to Kodak XAR-5 X-ray film at 70° C. using Kodak X-Omatic cassettes with regular intensifying screens. Under these conditions approximately 50 positive signals were found.

Example 7.4

Analysis of Phages Containing *T. reesei* xln A-related Sequences 18 of the hybridizing bacteriophage clones were purified as described in Example 3.2 and nine phages are selected and from these DNA is isolated as described in Example 3.3. The phages were analyzed by digestion of the DNA with HincII and HinfI. Based on the hybridization patterns found after Southern analysis (using the $^{32}$P labelled 900 bp XhoI/BamHI fragment as a probe, as described in Example 7.1), these phages were assigned to two classes: five of the analyzed phages as class A (phages 1, #3, #4, #20 and #22) and four as class B (phages #10, #16, #X$_2$ and #X$_3$). From each class, one phage was selected for further restriction analysis: phage #1 of class A and phage #10 of class B.

The phages #1 and #10 DNA were subjected to restriction analysis by digestion with BamHI, BglII, ECoRI, BglII and combinations thereof and by single digestions with KpnI, SmaI, XhoI, XbaI, SstI, HindIII and PstI. Southern analysis using the 900 bp XhoI/BamHI fragment as a probe was subsequently performed. On the basis of the patterns obtained, an approximately 6.5 kb BglII/SalI fragment from class A phage #1 and an approximately 7.5 kb BamHI/BglII fragment from class B phage #10 were chosen for subcloning.

The 6.5 kb BglII/SalI fragment was isolated and ligated as described in Example 3.5 into the BamHI/SalI-digested vector pEMBL18, resulting in the plasmid pIM030. *E. coli* JM109 containing plasmid pIM030 was deposited at the centraal Bureau voor Schimmelcultures, Baarn, The Netherlands on Jul. 11, 1991 and was assigned the designation CBS 420.91.

The 7.5 kb BamHI/BglII fragment was isolated and ligated, digested with BamHI and inserted into dephosphorylated vector pUC9, resulting in the plasmid pIM041. *E. coli* JM109 containing plasmid pIM041 was deposited at the Centraal Bureau voor Schimmelcultures, Baarn, The Netherlands on Jul. 11, 1991 and was assigned the designation CBS 421.91.

Both plasmids pIM030 and pIM041 were subjected to further restriction analysis, providing the restriction maps shown in FIGS. 19 and 20, respectively.

EXAMPLE 8

Application of the XYL A Protein in Animal Feed Compositions

The efficacy of endo-xylanase supplementation to a diet rich in wheat by-products on nutrient digestibility and zootechnical performance is demonstrated using the following experimental protocol.

One-day old female chicks were housed in battery cages with wire floors and fed on a commercial starter diet until the start of the experimental period. At day 13, the birds were allocated at random to equal live-weight treatment groups. Three different experimental diets were assigned to 18 groups of birds with 8 birds per group. The diets were pelleted under very mild conditions and the chicks were fed ad libitum during days 13 to 34 (post-hatching).

Feed consumption and growth were monitored weekly for each cage. Digestibility was measured by a 3 day excreta collection period. A semi-quantitative collection of the excreta was performed. Using a marker (HCL-insoluble ash), individual digestibility coefficients for protein, fat, crude fibre and Nitrogen Free Extract were calculated. The apparent metabolisable energy (AME) of each diet was calculated from the following equation:

$$AME\ (MJ/kg\ D.M.) = 17.46\ a_1 + 38.81\ a_2 + 8.0\ a_3 + 16.5\ a_4$$

$a_1 = $ crude protein (gram per kg $D.M.$) × $d.c.$[1)]

$a_2 = $ crude fat (gram per kg $D.M.$) × $d.c.$ $a_3 = $ crude fibre (gram per kg $D.M$) × $d.c.$ $a_4 = $ Nitrogen Free Extract (gram per kg $D.M.$) × $d.c.$

[1)] d.c. = digestibility coefficient

The basal diet was based on wheat bran, maize starch and protein-rich animal by-products (Table 3). To this diet, endo-xylanase was supplemented at two different levels, 36,000 U/kg and 174,000 U/kg purified endo-xylanase (specific activity 300,000 U/g).

TABLE 3

| Composition of the basal diet | |
|---|---|
| Ingredient | % |
| wheat bran | 40 |
| maize starch | 30 |
| maize | 4.4 |
| animal by-products (meat meal, fish meal, feather meal) | 9.7 |
| soy isolate (81% cp) | 6.0 |
| soy oil | 6.0 |
| fat blend | 0.7 |
| ground limestone | 0.32 |
| premix (including DL-methionine | 1.35 |

TABLE 3-continued

| Composition of the basal diet | |
|---|---|
| | % |
| & Lysine - HCL) | |
| SiO$_2$-marker (Diamol ®) | 1.4 |
| Calculated content | |
| AME (MJ/kg) | 12.66 |
| crude protein, % | 18.0 |
| lysine, % | 1.2 |
| methionine + cystine, % | 0.9 |
| Analyzed content | |
| crude protein, % | 18.2 |
| crude fat, % | 9.7 |
| crude fibre, % | 4.1 |
| SiO$_2$-marker, % | 1.07 |
| Ca, % | 0.8 |
| P, % | 0.85 |
| ash, % | 5.9 |

The most important results are summarized in Table 4 (performance data) and Table 5 (digestibility data). The performance data refer to the entire experimental period, days 13 to 34 (post-hatching), while the digestibility figures are the average values derived from analyses in excreta collected during days 21 to 24 and days 28 to 31.

TABLE 4

The effect of endoxylanase addition on chick performance from 13 to 34 days of age.

| Parameter | diet 1 basal | diet 2 36.000 U/kg endoxylanase | diet 3 174.000 U/kg endoxylanase |
|---|---|---|---|
| growth (g per day) | 50.5 | 50.8 | 51.9 |
| feed consumption (g/bird/day) | 95.6 | 89.7 | 92.6 |
| feed: gain (g:g) | 1.89 | 1.77 | 1.79 |

TABLE 5

The effect of endoxylanase addition of digestibility coefficients (d.c.) of the organic nutrients and calculated energy value of the diet.

| Digestibility coefficient | diet 1 = basal | diet 2 36,000 units/kg XYL A | diet 3 174,000 units/kg XYL A |
|---|---|---|---|
| crude protein*, % | 79 | 82 | 82 |
| crude fat, % | 85 | 91 | 82 |
| crude fibre, % | 0 | 11 | 11 |
| Nitrogen Free Extract, % | 73 | 75 | 75 |
| AME (MJ/kg D.M.) | 13.81 | 14.28 | 14.28 |

*The nitrogen measured in the excreta was corrected for the uric acid content in the urine.

This experiment demonstrates the efficacy of endoxylanase addition to feed compositions for broilers which contain a large proportion of wheat bran. Both the performance of the chicks and the energy value of the diets were affected positively.

Regarding the performance feed conversion, efficiency was the most sensitive parameter which reflected the influence of enzyme addition. There was a tendency towards a slightly reduced feed consumption in the enzyme supplemented groups associated with a similar or better growth. Consequently, the feed:gain ratio was decreased substantially.

The improvement in performance can be explained by the effects from enzyme addition on the digestibility coefficients. All nutrient digestibility figures were affected positively, although the increase in fat digestibility was most pronounced, which led to a 3.5% increase in the energy value of the enzyme-supplemented diets.

No dose-response relationship was noticed at these levels of enzyme inclusion.

EXAMPLE 9

The Use of Endo-xylanase in Bread Making

Pup-loaves were baked from 150 g dough pieces obtained by mixing 200 g wheat flour (100%), 106 ml water (53%), 1.2 g instant dry baker's yeast (0.6%: Gist-brocades N.V., Delft, The Netherlands), 4 g NaCl (2%), 400 mg $CaCl_2.2H_2O$ (0.2%), 10 mg fungal α-amylase P200 (Gist-brocades, 2250 SKB/kg flour) and a variable number of units of endoxylanase (xyl A) activity. After mixing for 6 minutes and 15 seconds at 52 r.p.m. in a pin mixer, the dough was divided, proofed for 45 minutes at 31°°C., punched, proofed for an additional 25 minutes, molded and panned. After a final proof of 70 minutes at 31°°C., the dough was baked for 20 minutes in an oven at 250° C. Loaf volume was determined by the rapeseed displacement method. The results are summarized in Table 6, below.

TABLE 6

Characteristics of bread prepared with various amounts of endo-xylanase (xyl A) activity

| Endo-xylanase activity (units) | Loaf volume (ml) | Break/ Shred* | Crumb Structure* |
|---|---|---|---|
| 0 | 546 | 6 | 6 |
| 32 | 560 | 7 | 6 |
| 128 | 579 | 7.5 | 7 |
| 320 | 609 | 8 | 6.5 |
| 640 | 621 | 7.5 | 6.5 |
| 960 | 624 | 7.5 | 7 |
| 2560 | 618 | 7.5 | 7.5 |

*= Score from 1 (lowest quality) to 10 (highest quality)

From these results, it is clear that an increasing amount of endo-xylanase activity added to the dough leads to an increase in loaf volume and an improvement of bread quality in terms of break and shred and crumb structure.

REFERENCES

Amons, R. (1987) FEBS Lett., 212, 68–72.
Biely, P., Mislovicova, D. and Toman, R. (1985a) Anal. Biochem, 144, 142–146.
Biely, P., Markovic, O. and Mislovicova, D. (1985b) Anal. Biochem, 144, 147–151.
Boel, E. et al. (1984a) EMBO J., 3, 1097–1102.
Boel, E. et al. (1984b) Moi. Cell. Biol., 4, 2306–2315.
Carré, B. and Brillouet, J. M. (1986) J. Science and Food Agric., 37, 341–351.
Chesson, A. (1987) Recent Advances in Animal Food Nutrition, Haresign, W. and Cole, D. J. A., eds., Butterworth, London, 71–89.
Cove, D. (1966) Biochem. Biophys. Acta 113, 51–56.
Dekker, R. F. A. and Richards, G. M. (1977) Adv. Carb. Chem. and Biochem., 32, 278–353.
Ehrlich, H. A., ed. (1989) PCR Technology: Principles and Applications for DNA Amplification, Stockton Press, New York.
Goosen, T., Bloemheuvel, G., Gysler, C., de Bie, D. A., van den Broek, H. W. J. and Swart, K. (1987) Curr. Genet., 11, 499–503.
Goosen, T., van Engelenburg, F., Debets, F., Swart, K., Bos, K. and van den Broek, H. W. J. (1989) Mol. Gen. Genet., 219, 282–288.
de Graaff, L. H., van den Broek, H. W. J. and Visser, J. (1988) Curt. Genet., 13, 315–321.
Kelly, J. and Hynes, M. (1985) EMBO J. 4, 475–479.
Kusters-van Someten, M. A., Samson, R. A. and Visser, J. (1991) Curr. Genet., 19, 21.
Laemmli, U.K. (1970) Nature 227, 680–685.
Leathers, T. D., Kurtzman, C. P., Detroy, R. W. (1984) Biotechnol. Bioeng. Symp., 14, 225.
Maniatis T., E. F. Fritsch, J. Sambrook (1982) *Molecular Cloning, A Laboratory Manual*, Cold Spring Harbor Laboratory, N.Y.
Matsudaira, P. (1987) J. Biol. Chem., 262, 10035–10038.
McCleary, B. V. and Matheson, N. K. (1986) Adv. Carb. Chem. and Biochem., 44, 147–276.
Messing, J. (1983) Methods in Enzymology, 101C, 20–78.
Moonen, J. H. E., Scheepstra, A., Graveland, A. (1982) Euphitica, 31, 677.
Murray, N. (1977) Mol. Gen. Genet., 150, 53–58.
Norrander, J., Kempe, T. and Messing, J. (1983) Gene, 26, 101–106.
Poutanen, K. and Puls, J. (1988) Appl. Microbiol. Biotechnol., 28, 425.
Saiki, R. K. et al. (1988) Science, 239, 487–491.
Sanger, F., Nickelen, S. and Coulson, A. R. (1977) Proc. Natl. Acad. Sci. USA, 74, 5463–5467.
Tilburn, J. et.al. (1983) Gene 26, 205–221.
Vieirra, J. and Messing, J. (1982) Gene, 19, 259–268.
Visniac, W. and Santer, M. (1957) Bact. Rev., 21, 195–213.
Wernars, K. (1986) Thesis, Agricultural University, Wageningen, The Netherlands.
Wong, K. K. Y., et al. (1988) Microbiol. Rev., 52, 305–317.
Woodward, G. (1984) Topics in Enzyme Ferment. Biotechnol., 8, 9–30.
Yanisch-Perron, C., Viera, J. and Messing, J. (1985) Gene, 33, 103–109.

We claim:

1. A DNA molecule in purified and isolated form that comprises a coding region that encodes a fungal endoxylanase, wherein said fungal endo-xylanase has the amino acid sequence shown as positions 1–184 in SEQ ID:1 or is encoded by a nucleotide sequence that hybridizes to the DNA of SEQ ID:1 under stringency conditions equivalent to those in two washes in 5×SSC, 0.1% SDS at 60° C. followed by two washes in 3×SSC at 60° C.

2. The DNA molecule of claim 1 which further includes, upstream of said coding region, a nucleotide sequence that encodes the amino acid sequence shown as positions −27 to −1 in SEQ ID:1 or which is encoded by a DNA that hybridizes to the DNA shown as encoding positions −27 to −1 of SEQ ID:1 under conditions of stringency equivalent to those in two washes in 5×SSC, 0.1% SDS at 60° C. followed by two washes in 3×SSC at 60° C.

3. The DNA of claim 1 which has operably linked upstream of said coding region the nucleotide sequence shown as positions 1–949 of SEQ ID:1 or a nucleotide sequence which hybridizes to the nucleotide sequence shown as positions 1–949 of SEQ ID:1 under conditions of stringency equivalent to those in two washes in 5×SSC, 0.1% SDS at 60° C. followed by two washes in 3×SSC at 60° C.

4. A recombinant DNA molecule capable of effecting expression of a coding region encoding a fungal endo-xylanase wherein said fungal endo-xylanase has the amino acid sequence shown as positions 1–184 in SEQ ID:1 or is encoded by a nucleotide sequence that hybridizes to the DNA of SEQ ID:1 under stringency conditions equivalent to those in two washes in 5×SSC, 0.1% SDS at 60° C. followed by two washes in 3×SSC at 60° C.;
which DNA molecule comprises said coding region operably linked to control sequences capable of effecting expression of the coding region, wherein said DNA molecule further comprises at least one nucleotide control sequence heterologous to said coding region.

5. The recombinant DNA molecule of claim 4 wherein said control sequences comprise a promoter and wherein said promoter is an amyloglucosidase promoter or a xylanase promoter.

6. The recombinant DNA molecule of claim 4 wherein said coding region is preceded by and operably linked to a secretion leader sequence of an amyloglucosidase or a xylanase.

7. A microbial host cell which contains the DNA molecule of any of claims 4–6.

8. The host cell of claim 7 which is selected from the group consisting of Aspergillus, Kluyveromyces, Trichoderma, Saccharomyces and Bacillus.

9. The host cell of claim 8 wherein said host is selected from the group consisting of *Aspergillus tubigensis, Aspergillus niger, Aspergillus awanori, Aspergillus aculeatus, Aspergillus oryzae, Trichoderma reesei, Bacillus subtilis, Bacillus licheniformis, Kluyveromyces lactis* and *Saccharomyces cerevisiae.*

10. A method to produce an endo-xylanase which method comprises culturing the host cell of claim 9 under conditions favorable to expression of said coding region to produce said endo-xylanase; and
recovering the endo-xylanase from the culture.

11. A fungal endo-xylanase in purified and isolated form which fungal endo-xylanase has the amino acid sequence shown as positions 1–184 in SEQ ID:1 or is encoded by a nucleotide sequence that hybridizes to the DNA of SEQ ID:1 under stringency conditions equivalent to those in two washes in 5×SSC, 0.1% SDS at 60° C. followed by two washes in 3×SSC at 60° C.

12. A method to degrade a xylan-containing substrate which method comprises treating said substrate with the endo-xylanase of claim 11.

13. A method to prepare an animal foodstuff which method comprises adding to said foodstuff mixture the endoxylanase of claim 11.

14. An animal feed composition which comprises the endo-xylanase of claim 11.

15. A method to prepare a bread dough which method comprises adding to said bread dough the endoxylanase of claim 11.

16. A bread dough which comprises the endoxylanase of claim 11.

17. A method to remove lignins from kraft pulp which method comprises treating said kraft pulp with an effective amount of the endo-xylanase of claim 11.

18. A kraft pulp prepared by the method of claim 17.

19. A DNA molecule in purified and isolated form which comprises an effective regulatory portion of the nucleotide sequence of SEQ ID:1 at positions 1–949.

* * * * *

Adverse Decisions In Interference

Patent No. 5,358,864, Henriette C. Van Den Broeck, Leendert H. DeGraaff, Jan D. R. Hille, Albert J. J. Van Ooyen, Jacob Visser, Abraham Harder, CLONING AND EXPRESSION OF XYLANASE GENES FROM FUNGAL ORIGIN, Interference No. 103,637, final judgment adverse to the patentees rendered July 10, 2001, as to claims 1-19.

*(Official Gazette August 7, 2001)*